(12) United States Patent
Shinno et al.

(10) Patent No.: US 9,804,115 B2
(45) Date of Patent: Oct. 31, 2017

(54) BIOLOGICAL INFORMATION MEASUREMENT DEVICE, AND BIOLOGICAL INFORMATION MEASUREMENT METHOD USING SAME

(71) Applicant: Panasonic Healthcare Holdings Co., Ltd., Tokyo (JP)

(72) Inventors: Teppei Shinno, Ehime (JP); Shouko Hironaka, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 0 days.

(21) Appl. No.: 15/456,093

(22) Filed: Mar. 10, 2017

(65) Prior Publication Data

US 2017/0234824 A1   Aug. 17, 2017

Related U.S. Application Data

(63) Continuation of application No. 14/389,175, filed as application No. PCT/JP2013/002609 on Apr. 17, 2013, now Pat. No. 9,625,442.

(30) Foreign Application Priority Data

Apr. 19, 2012 (JP) ................. 2012-095327

(51) Int. Cl.
   *G01N 33/49*      (2006.01)
   *G01N 27/327*     (2006.01)
   *C12Q 1/00*       (2006.01)

(52) U.S. Cl.
   CPC ........ *G01N 27/3274* (2013.01); *C12Q 1/006* (2013.01); *G01N 27/3272* (2013.01); *G01N 33/49* (2013.01)

(58) Field of Classification Search
   CPC ........ G01N 27/3274; G01N 33/48707; G01N 33/49; G01N 33/50; G01N 33/66
   See application file for complete search history.

(56) References Cited

U.S. PATENT DOCUMENTS

| 5,411,029 A | 5/1995 | Hirai |
| 5,803,908 A | 9/1998 | Steuer |

(Continued)

FOREIGN PATENT DOCUMENTS

| DE | 691 33 252 | 1/2004 |
| EP | 2 306 190 | 9/2010 |

(Continued)

OTHER PUBLICATIONS

Extended European Search Report issued for corresponding European Patent Application No. 13778180.3, dated Mar. 18, 2015.

*Primary Examiner* — Francis Gray
(74) *Attorney, Agent, or Firm* — Hamre, Schumann, Mueller & Larson, P.C.

(57) ABSTRACT

The present invention has an object of improving the measurement accuracy in a biological information measurement device, e.g., for measuring a blood glucose level. The device is configured to be able to change at least one of i) a voltage value to be applied to the second input terminal and the third input terminal (i.e., the blood component measurement counter electrode 7 and the blood component measurement working electrode 6) in the second biological information measurement mode D and ii) a voltage application time during which a voltage is applied to the second input terminal and the third input terminal in the second biological information measurement mode D based on the first biological information in the first biological information measurement mode A. A hematocrit value is measured in the first biological information measurement mode A, and a glucose (Continued)

value is measured based on the hematocrit value in the second biological information measurement mode D.

3 Claims, 16 Drawing Sheets

(56) References Cited

U.S. PATENT DOCUMENTS

| | | | |
|---|---|---|---|
| 8,137,529 B2 * | 3/2012 | Huang | C12Q 1/006 205/775 |
| 8,308,935 B2 * | 11/2012 | Chen | A61B 5/14532 204/403.02 |
| 8,709,232 B2 * | 4/2014 | Matzinger | G01N 27/3274 204/403.01 |
| 2005/0067301 A1 | 3/2005 | Morita et al. | |
| 2007/0131565 A1 | 6/2007 | Fujiwara et al. | |
| 2007/0138026 A1 | 6/2007 | Fujiwara et al. | |
| 2008/0083618 A1 | 4/2008 | Neel et al. | |
| 2009/0184004 A1 | 7/2009 | Chatelier et al. | |
| 2010/0140087 A1 * | 6/2010 | Ueno | C12Q 1/001 204/403.01 |
| 2010/0243476 A1 | 9/2010 | Fujiwara et al. | |
| 2010/0283488 A1 * | 11/2010 | Nakamura | G01N 27/327 324/692 |
| 2011/0203942 A1 * | 8/2011 | Uchiyama | G01N 27/3274 205/782 |
| 2013/0105334 A1 * | 5/2013 | Nakamura | G01N 27/327 205/792 |
| 2014/0224672 A1 * | 8/2014 | Hsu | C12Q 1/001 205/777.5 |
| 2015/0068926 A1 * | 3/2015 | Ainger | G01N 27/3271 205/792 |

FOREIGN PATENT DOCUMENTS

| | | |
|---|---|---|
| JP | 2005-147990 | 6/2005 |
| JP | 2011-033638 | 2/2011 |
| JP | 2011-075362 | 4/2011 |
| JP | 2011-164116 | 8/2011 |
| WO | 92/01928 | 2/1992 |
| WO | 03/044513 | 5/2003 |
| WO | 2005/054840 | 6/2005 |
| WO | 2008/030757 | 3/2008 |
| WO | 2008/047843 | 4/2008 |
| WO | 2009/119118 | 10/2009 |
| WO | 2010/061629 | 6/2010 |

* cited by examiner

BIOLOGICAL INFORMATION MEASUREMENT DEVICE, AND BIOLOGICAL INFORMATION MEASUREMENT METHOD USING SAME

TECHNICAL FIELD

The present invention relates to a biological information measurement device, e.g., for measuring a blood glucose level and a biological information measurement method using the biological information measurement device.

BACKGROUND ART

A conventional biological information measurement device, e.g., for measuring a blood glucose level has the following configuration.

The conventional biological information measurement device to which a biosensor is to be attached, the biosensor including a first electrode, a second electrode, a third electrode, and a reagent portion provided between the second electrode and the third electrode, includes the following: a first input terminal to be connected to the first electrode; a second input terminal to be connected to the second electrode; a third input terminal to be connected to the third electrode; a voltage application portion that applies a voltage to the first input terminal, the second input terminal, and the third input terminal; a determination portion that is connected to the first input terminal, the second input terminal, and the third input terminal; a control portion that is connected to the determination portion and the voltage application portion; and a display portion that is connected to the control portion (see, e.g., Patent Document 1).

PRIOR ART DOCUMENTS

Patent Documents

Patent Document 1: WO 2008/047843 A1

DISCLOSURE OF INVENTION

Problem to be Solved by the Invention

In the above conventional example, the biosensor is attached to the biological information measurement device, and then a drop of blood (i.e., a biological sample) is placed on the biosensor. Subsequently, a blood glucose level is measured as biological information.

In this case, the blood glucose level to be measured varies depending on hematocrit of the blood. Therefore, in the conventional example, a hematocrit value is measured after measuring the blood glucose level, and then the blood glucose level is corrected in accordance with the hematocrit value and displayed on the display portion.

However, such a measurement may reduce the measurement accuracy of the blood glucose level due to the hematocrit value.

The blood glucose level is significantly affected by the hematocrit value even while it is being measured. After that, if the significantly affected blood glucose level is tried to be corrected in accordance with the hematocrit value, the amount of correction to the final blood glucose level is increased. This results in low measurement accuracy of the corrected blood glucose level.

With the foregoing in mind, it is an object of the present invention to improve the measurement accuracy of the biological information.

Means for Solving Problem

To achieve the above object, the present invention is directed to a biological information measurement device to which a biosensor is to be attached. The biosensor includes a first electrode, a second electrode, a third electrode, and a reagent portion provided between the second electrode and the third electrode. The biological information measurement device includes the following: a first input terminal to be connected to the first electrode; a second input terminal to be connected to the second electrode; a third input terminal to be connected to the third electrode; a voltage application portion that applies a voltage to the first input terminal, the second input terminal, and the third input terminal; a control portion that is connected to the voltage application portion; and a display portion that is connected to the control portion. The control portion is configured to perform a first biological information measurement mode in which first biological information is measured based on a current flowing through the first input terminal and a second biological information measurement mode in which second biological information is measured by applying a voltage to the second input terminal and the third input terminal after the first biological information measurement mode. The display portion is configured to display the second biological information. The control portion is configured to be able to change at least one of i) a voltage value to be applied to the second input terminal and the third input terminal in the second biological information measurement mode and ii) a voltage application time during which a voltage is applied to the second input terminal and the third input terminal in the second biological information measurement mode based on the first biological information in the first biological information measurement mode.

Moreover, the present invention is directed to a biological information measurement device to which a biosensor is to be attached. The biosensor includes a first electrode, a second electrode, a third electrode, and a reagent portion provided between the second electrode and the third electrode. The biological information measurement device includes the following: a first input terminal to be connected to the first electrode; a second input terminal to be connected to the second electrode; a third input terminal to be connected to the third electrode; a voltage application portion that applies a voltage to the first input terminal, the second input terminal, and the third input terminal; a control portion that is connected to the voltage application portion; and a display portion that is connected to the control portion. The control portion is configured to perform a first biological information measurement mode in which first biological information is measured based on a current flowing through the first input terminal, a pre-processing application mode in which a voltage is applied to the second input terminal and the third input terminal after the first biological information measurement mode, a voltage application stop mode in which the application of the voltage to the second input terminal and the third input terminal is stopped after the pre-processing application mode, and a second biological information measurement mode in which second biological information is measured by applying a voltage to the second input terminal and the third input terminal after the voltage application stop mode. The display portion is configured to display the second biological information. The control portion is configured to be able to change a voltage value to be applied to the second input terminal and the third input terminal in the pre-processing application mode based on the first biological information in the first biological information measurement mode.

Further, the present invention is directed to a biological information measurement device to which a biosensor is to be attached. The biosensor includes a first electrode, a second electrode, a third electrode, and a reagent portion provided between the second electrode and the third electrode. The biological information measurement device includes the following: a first input terminal to be connected to the first electrode; a second input terminal to be connected to the second electrode; a third input terminal to be connected to the third electrode; a voltage application portion that applies a voltage to the first input terminal, the second input terminal, and the third input terminal; a control portion that is connected to the voltage application portion; and a display portion that is connected to the control portion. The control portion is configured to perform a first biological information measurement mode in which first biological information is measured based on a current flowing through the first input terminal, a pre-processing application mode in which a voltage is applied to the second input terminal and the third input terminal after the first biological information measurement mode, a voltage application stop mode in which the application of the voltage to the second input terminal and the third input terminal is stopped after the pre-processing application mode, and a second biological information measurement mode in which second biological information is measured by applying a voltage to the second input terminal and the third input terminal after the voltage application stop mode. The display portion is configured to display the second biological information. The control portion is configured to be able to change a voltage value to be applied to the second input terminal and the third input terminal in the pre-processing application mode based on the first biological information in the first biological information measurement mode. The control portion is configured to be able to change a voltage application time during which a voltage is applied to the second input terminal and the third input terminal in the second biological information measurement mode based on the first biological information in the first biological information measurement mode.

With these configurations, the present invention can achieve the intended purpose of improving the measurement accuracy of the biological information.

Effects of the Invention

As described above, the present invention is directed to a biological information measurement device to which a biosensor is to be attached. The biosensor includes a first electrode, a second electrode, a third electrode, and a reagent portion provided between the second electrode and the third electrode. The biological information measurement device includes the following: a first input terminal to be connected to the first electrode; a second input terminal to be connected to the second electrode; a third input terminal to be connected to the third electrode; a voltage application portion that applies a voltage to the first input terminal, the second input terminal, and the third input terminal; a control portion that is connected to the voltage application portion; and a display portion that is connected to the control portion. The control portion is configured to perform a first biological information measurement mode in which first biological information is measured based on a current flowing through the first input terminal and a second biological information measurement mode in which second biological information is measured by applying a voltage to the second input terminal and the third input terminal after the first biological information measurement mode. The display portion is configured to display the second biological information. The control portion is configured to be able to change at least one of i) a voltage value to be applied to the second input terminal and the third input terminal in the second biological information measurement mode and a voltage application time during which a voltage is applied to the second input terminal and the third input terminal in the second biological information measurement mode based on the first biological information in the first biological information measurement mode. Thus, the present invention can improve the measurement accuracy.

According to the present invention, at least one of the voltage value to be applied to the second input terminal and the third input terminal in the second biological information measurement mode and the voltage application time during which a voltage is applied to the second input terminal and the third input terminal in the second biological information measurement mode can be changed based on the first biological information in the first biological information measurement mode. The first biological information, e.g., a hematocrit value is measured in the first biological information measurement mode, and the second biological information, e.g., a blood glucose level is measured based on this hematocrit value in the second biological information measurement mode.

As described above, the present invention is directed to a biological information measurement device to which a biosensor is to be attached. The biosensor includes a first electrode, a second electrode, a third electrode, and a reagent portion provided between the second electrode and the third electrode. The biological information measurement device includes the following: a first input terminal to be connected to the first electrode; a second input terminal to be connected to the second electrode; a third input terminal to be connected to the third electrode; a voltage application portion that applies a voltage to the first input terminal, the second input terminal, and the third input terminal; a control portion that is connected to the voltage application portion; and a display portion that is connected to the control portion. The control portion is configured to perform a first biological information measurement mode in which first biological information is measured based on a current flowing through the first input terminal, a pre-processing application mode in which a voltage is applied to the second input terminal and the third input terminal after the first biological information measurement mode, a voltage application stop mode in which the application of the voltage to the second input terminal and the third input terminal is stopped after the pre-processing application mode, and a second biological information measurement mode in which second biological information is measured by applying a voltage to the second input terminal and the third input terminal after the voltage application stop mode. The display portion is configured to display the second biological information. The control portion is configured to be able to change a voltage value to be applied to the second input terminal and the third input terminal in the pre-processing application mode based on the first biological information in the first biological information measurement mode. Thus, the present invention can improve the measurement accuracy.

According to the present invention, the voltage value to be applied to the second input terminal and the third input terminal in the pre-processing application mode can be changed based on the first biological information in the first biological information measurement mode. The first biological information, e.g., a hematocrit value is measured in the first biological information measurement mode, and the second biological information, e.g., a blood glucose level is measured based on this hematocrit value in the second biological information measurement mode.

As described above, the present invention is directed to a biological information measurement device to which a biosensor is to be attached. The biosensor includes a first electrode, a second electrode, a third electrode, and a reagent portion provided between the second electrode and the third electrode. The biological information measurement device includes the following: a first input terminal to be connected to the first electrode; a second input terminal to be connected to the second electrode; a third input terminal to be connected to the third electrode; a voltage application portion that applies a voltage to the first input terminal, the second input terminal, and the third input terminal; a control portion that is connected to the voltage application portion; and a display portion that is connected to the control portion. The control portion is configured to perform a first biological information measurement mode in which first biological information is measured based on a current flowing through the first input terminal, a pre-processing application mode in which a voltage is applied to the second input terminal and the third input terminal after the first biological information measurement mode, a voltage application stop mode in which the application of the voltage to the second input terminal and the third input terminal is stopped after the pre-processing application mode, and a second biological information measurement mode in which second biological information is measured by applying a voltage to the second input terminal and the third input terminal after the voltage application stop mode. The display portion is configured to display the second biological information. The control portion is configured to be able to change a voltage value to be applied to the second input terminal and the third input terminal in the pre-processing application mode based on the first biological information in the first biological information measurement mode. The control portion is configured to be able to change a voltage application time during which a voltage is applied to the second input terminal and the third input terminal in the second biological information measurement mode based on the first biological information in the first biological information measurement mode. Thus, the present invention can improve the measurement accuracy.

According to the present invention, the voltage value to be applied to the second input terminal and the third input terminal in the pre-processing application mode can be changed based on the first biological information in the first biological information measurement mode, and the voltage application time during which a voltage is applied to the second input terminal and the third input terminal in the second biological information measurement mode can be changed based on the first biological information in the first biological information measurement mode. The first biological information, e.g., a hematocrit value is measured in the first biological information measurement mode, and the second biological information, e.g., a blood glucose level is measured based on this hematocrit value in the second biological information measurement mode.

Therefore, according to the present invention, since the second biological information (e.g., the blood glucose level) itself is measured under the conditions that are not much affected by the first biological information (e.g., the hematocrit value), the measurement accuracy can be improved.

DESCRIPTION OF THE INVENTION

Hereinafter, an embodiment of the present invention that is applied to a biological information measurement device for measuring a blood glucose level will be described with reference to the accompanying drawings.

Embodiment 1

Figure 1:
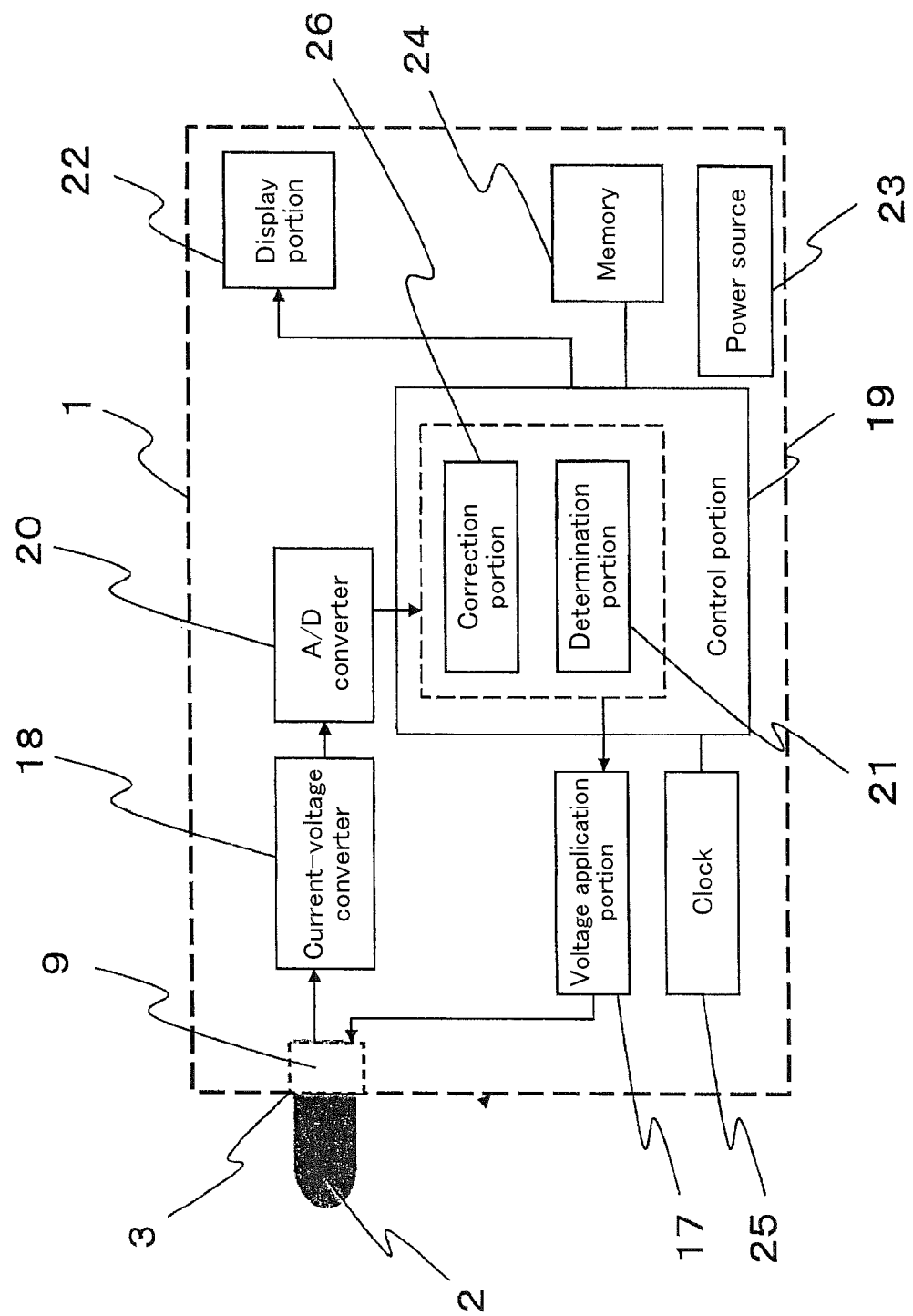
FIG. 1 is an electrical block diagram of a biological information measurement device of an embodiment of the present invention.

FIG. 1 is an electrical block diagram of a biological information measurement device of an embodiment of the present invention. FIG. 2A is an exploded perspective view of a biosensor used for a biological information measurement device of an embodiment of the present invention. FIG. 2B is a cross-sectional view of a biosensor used for a biological information measurement device of an embodiment of the present invention. As shown in FIG. 1, an insertion port 3 for a biosensor 2 is provided at one end of a main body case 1 of the biological information measurement device.

As shown in an example of FIG. 2A, the biosensor 2 includes a rectangular insulating substrate 4 and four electrodes formed on the insulating substrate 4. The four electrodes, i.e., a hematocrit measurement working electrode (an example of a first electrode) 5, a blood component measurement working electrode (an example of a third electrode) 6, a blood component measurement counter electrode (an example of a second electrode) 7, and a blood component introduction detecting electrode 8 are arranged opposite each other with a predetermined space between them. Examples of the biological information to be measured by the biological information measurement device of the present invention include a glucose value, a lactic acid value, a uric acid value, a bilirubin value, and a cholesterol value. Biological samples used to obtain the biological information may be, e.g., blood, urine, and sweat. The biosensor 2 is an example when the biological sample is blood.

In the biosensor 2, each of the hematocrit measurement working electrode 5, the blood component measurement working electrode 6, the blood component measurement counter electrode 7, and the blood component introduction detecting electrode 8 at one end of the insulating substrate 4 (i.e., at the right end of FIG. 2) comes into contact with an input terminal portion 9 shown in FIG. 1, so that the biosensor 2 is electrically connected to the biological information measurement device.

The biosensor 2 further includes a reagent portion 10 provided on an electrode portion that is formed of the blood component measurement working electrode 6, the blood component measurement counter electrode 7, and the blood component introduction detecting electrode 8.

In the biosensor 2, a reagent 11 is placed in the reagent portion 10. The reagent 11 contains an oxidoreductase such as glucose dehydrogenase and a mediator (electron carrier), and selectively contains a polymeric material, an enzyme stabilizer, and a crystal homogenizing agent as optional components. In the biosensor 2, a cover 13 is disposed on the insulating substrate 4 and the reagent 11 via a spacer 12, while leaving one end of the insulating substrate 4 uncovered.

The spacer 12 of the biosensor 2 has a blood supply path 14 for introducing blood. The blood supply path 14 extends from the other end of the biosensor 2 (i.e., the left end of FIG. 2) to the position above the reagent 11. The other end of the blood supply path 14 is open to the outside and serves as a blood inlet 15.

The hematocrit measurement working electrode 5, the blood component measurement working electrode 6, the blood component measurement counter electrode 7, and the blood component introduction detecting electrode 8 extend to one end of the biosensor 2 (i.e., the right end of FIG. 2), where the portions of the hematocrit measurement working electrode 5, the blood component measurement working electrode 6, the blood component measurement counter electrode 7, and the blood component introduction detecting electrode 8 are not covered with the cover 13 and exposed.

Moreover, one end of each of these electrodes is connected to the input terminal portion 9 shown in FIG. 1.

Specifically, in the biosensor 2, the hematocrit measurement working electrode 5 is connected to a first input terminal (not shown) of the input terminal portion 9, the blood component measurement working electrode 6 is connected to a third input terminal (not shown) of the input terminal portion 9, the blood component measurement counter electrode 7 is connected to a second input terminal (not shown) of the input terminal portion 9, and the blood component introduction detecting electrode 8 is connected to a fourth input terminal (not shown) of the input terminal portion 9.

Figure 2:
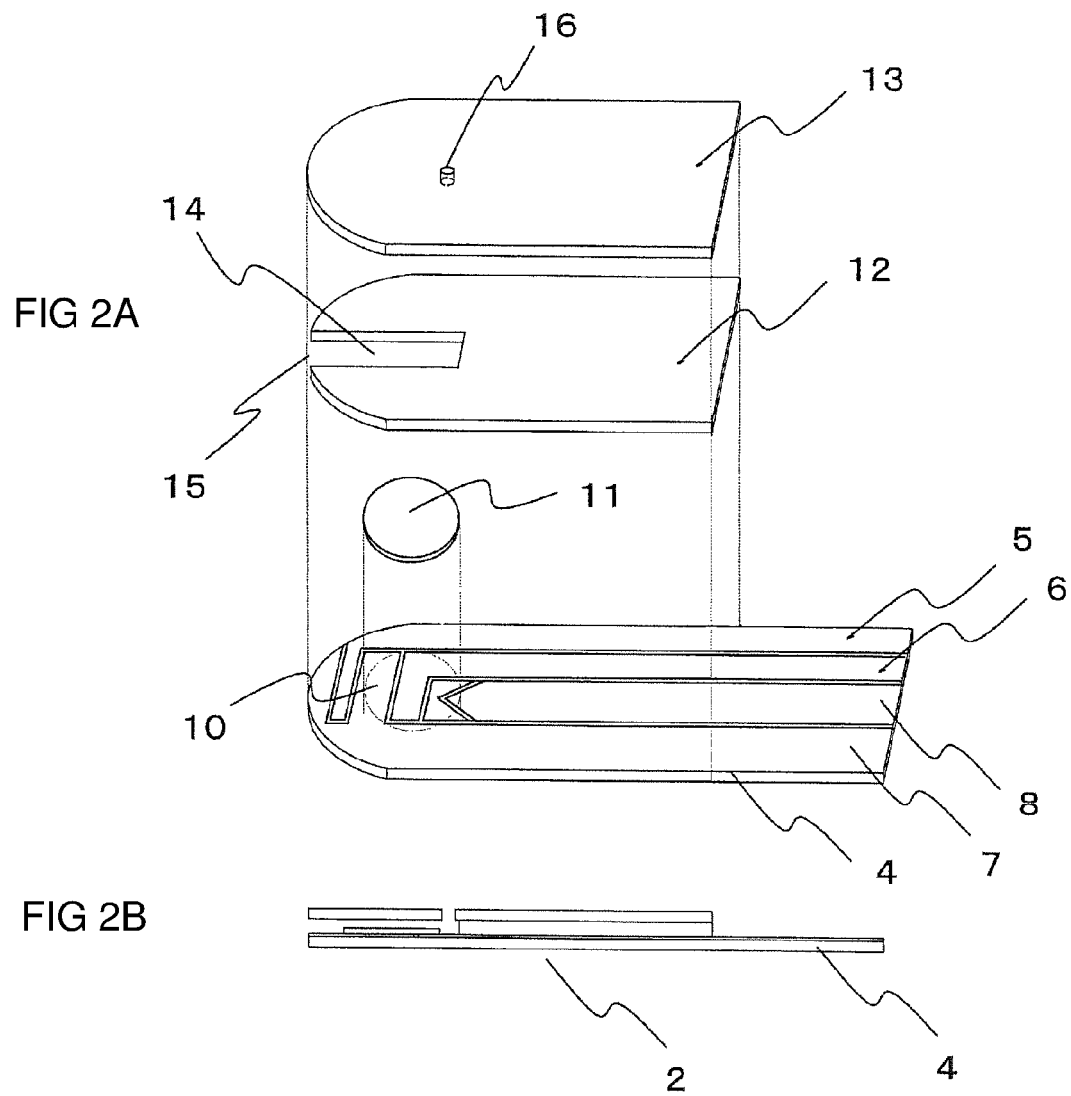
FIG. 2A is an exploded perspective view of a biosensor used for a biological information measurement device of an embodiment of the present invention.
FIG. 2B is a cross-sectional view of a biosensor used for a biological information measurement device of an embodiment of the present invention.

As can also be seen from FIG. 2, in the biosensor 2, the hematocrit measurement working electrode 5 is located closest to the blood inlet 15, followed by the blood component measurement counter electrode 7, the blood component measurement working electrode 6, and the blood component introduction detecting electrode 8.

That is, in the biosensor 2, the hematocrit measurement working electrode (an example of the first electrode) 5, the blood component measurement counter electrode (an example of the second electrode) 7, the blood component measurement working electrode (an example of the third electrode) 6, and the blood component introduction detecting electrode 8 are arranged in this order from the blood inlet 15 side.

The cover 13 of the biosensor 2 has an air hole 16 in order to promote a capillary action when a drop of blood is placed on the blood inlet 15 and to allow the blood to come into the blood component introduction detecting electrode 8.

Next, the configuration of the biosensor 2 will be described in more detail.

In the present invention, the material of the insulating substrate 4 is not particularly limited and may be, e.g., polyethylene terephthalate (PET), polycarbonate (PC), polyimide (PI), polyethylene (PE), polypropylene (PP), polystyrene (PS), polyvinyl chloride (PVC), polyoxymethylene (POM), monomer-cast nylon (MC), polybutylene terephthalate (PBT), methacrylate resin (PMMA), ABS resin (ABS), or glass. Among them, polyethylene terephthalate (PET), polycarbonate (PC), polyimide (PI) are preferred, and polyethylene terephthalate (PET) is more preferred.

The size of the insulating substrate 4 is not particularly limited. For example, the insulating substrate 4 has a total length of 5 to 100 mm, a width of 2 to 50 mm, and a thickness of 0.05 to 2 mm, preferably has a total length of 7 to 50 mm, a width of 3 to 20 mm, and a thickness of 0.1 to 1 mm, and more preferably has a total length of 10 to 30 mm, a width of 3 to 10 mm, and a thickness of 0.1 to 0.6 mm.

The electrodes on the insulating substrate 4 can be produced, e.g., using a material such as gold, platinum, or palladium, forming a conductive layer by sputtering or evaporation, and processing the conductive layer into a particular electrode pattern with a laser. The laser may be, e.g., a YAG laser, a $CO_2$ laser, or an excimer laser. The electrode pattern is not limited to that disclosed in the present invention, and any electrode pattern is available as long as it can achieve the effects of the present invention. The electrodes of the biosensor 2 used in the present invention may be coated with a polymeric material in order to prevent adhesion of impurities, oxidation, or the like. The coating on the surface of the electrodes can be performed, e.g., by preparing a solution of the polymeric material, dropping or applying the solution to the surface of the electrodes, and drying the solution. The drying process may be, e.g., natural drying, air drying, hot air drying, or drying by heating.

The electron carrier of the biosensor 2 is not particularly limited and may be, e.g., ferricyanide, p-benzoquinone, p-benzoquinone derivative, phenazine methosulfate, methylene blue, ferrocene, or ferrocene derivative. Among them, ferricyanide is preferred, and potassium ferricyanide is more preferred. The amount of the electron carrier to be mixed is not particularly limited and may be, e.g., 0.1 to 1000 mM, preferably 1 to 500 mM, and more preferably 10 to 200 mM per one measurement or one biosensor.

In the present invention, the first biological information is, e.g., a hematocrit value, and the second biological information is, e.g., a glucose value, a lactic acid value, a uric acid value, a bilirubin value, or a cholesterol value. The oxidoreductase of the present invention may be appropriately selected according to the type of the second biological information. Examples of the oxidoreductase include glucose oxidase, lactate oxidase, cholesterol oxidase, bilirubin oxidase, glucose dehydrogenase, and lactate dehydrogenase. The amount of the oxidoreductase is, e.g., 0.01 to 100 U, preferably 0.05 to 10 U, and more preferably 0.1 to 5 U per one sensor or one measurement. In particular, the glucose value is preferred as the second biological information, and the glucose oxidase and the glucose dehydrogenase are preferred as the oxidoreductase.

The reagent 11 of the present invention can be produced in the following manner. For example, 0.1 to 5.0 U per sensor of flavin adenosine dinucleotide-dependent glucose dehydrogenase (FAD-GDH), 10 to 200 mM of potassium ferricyanide, 1 to 50 mM of maltitol, and 20 to 200 mM of taurine are added to and dissolved in a 0.01 to 2.0 wt % carboxymethyl cellulose (CMC) aqueous solution to prepare a reagent solution. Then, the reagent solution is dropped onto the electrodes of the insulating substrate 4 and dried.

Next, in the present invention, the material of the spacer 12 is not particularly limited and may be, e.g., the same as that of the insulating substrate 4. The size of the spacer 12 is not particularly limited. For example, the spacer 12 has a total length of 5 to 100 mm, a width of 2 to 50 mm, and a thickness of 0.01 to 1 mm, preferably has a total length of 7 to 50 mm, a width of 3 to 20 mm, and a thickness of 0.05 to 0.5 mm, and more preferably has a total length of 10 to 30 mm, a width of 3 to 10 mm, and a thickness of 0.05 to 0.25 mm. The spacer 12 has an I-shaped notch that serves as the blood supply path 14 for introducing blood. The blood supply path 14 may be, e.g., in the form of a T-shaped notch. In such a case, the present invention can also be carried out by appropriately providing a reagent portion and an electrode portion at each end of the blood supply path to perform a hematocrit measurement and a glucose measurement separately.

In the present invention, the material of the cover 13 is not particularly limited and may be, e.g., the same as that of the insulating substrate 4. It is more preferable that a portion of the cover 13 that forms the ceiling of the blood supply path 14 is subjected to a hydrophilic treatment. The hydrophilic treatment may be, e.g., a method for applying a surface active agent or a method for introducing a hydrophilic functional group such as a hydroxyl group, a carbonyl group, or a carboxyl group into the surface of the cover 13 by plasma processing. The size of the cover 13 is not particularly limited. For example, the cover 13 has a total length of 5 to 100 mm, a width of 3 to 50 mm, and a thickness of 0.01 to 0.5 mm, preferably has a total length of 10 to 50 mm, a width of 3 to 20 mm, and a thickness of 0.05 to 0.25 mm, and more preferably has a total length of 15 to 30 mm, a width of 5 to 10 mm, and a thickness of 0.05 to 0.1 mm. The cover 13 preferably has the air hole 16, e.g., in the form of a circle, ellipse, or polygon. The air hole 16 may have, e.g., a maximum diameter of 0.01 to 10 mm, preferably a maximum diameter of 0.05 to 5 mm, and more preferably a maximum diameter of 0.1 to 2 mm. The air hole 16 may be formed, e.g., by punching through the cover 13 with a laser or drill, or by using a die that enables an air vent to be provided during the formation of the cover 13.

Next, as shown in FIG. 2, the insulating substrate 4, the spacer 12, and the cover 13 are laminated in this order and integrated into one component, thereby producing the biosensor 2. For the integration, the three members may be joined using an adhesive or thermally fused together. Examples of the adhesive include an epoxy adhesive, an acrylic adhesive, a polyurethane adhesive, a thermosetting adhesive (such as a hot-melt adhesive), and a UV curable adhesive.

Referring back to FIG. 1 again, a voltage application portion 17 for applying a voltage and a current-voltage converter 18 are connected to the input terminal portion 9 of the biological information measurement device of an embodiment of the present invention.

A voltage is supplied from a control portion 19 to the voltage application portion 17, and this voltage is then applied via the input terminal portion 9 to a desired electrode among the hematocrit measurement working electrode 5, the blood component measurement working electrode 6, the blood component measurement counter electrode 7, and the blood component introduction detecting electrode 8 of the biosensor 2 for a predetermined time. The current flowing between the electrodes of the biosensor 2 as a result of this voltage application is converted to a voltage by the current-voltage converter 18, and subsequently the voltage is converted to a digital value by an analog-digital (A/D) converter 20. Thereafter, a determination portion 21 compares the digitized voltage value with a threshold value.

A display portion 22 is connected to the control portion 19 and displays the glucose value detected by the biosensor 2 and the results of the determination made by the determination portion 21.

In FIG. 1, reference numeral 23 denotes a power source that supplies power to each portion. Reference numeral 24 denotes a memory that stores a table containing hematocrit values (the first biological information) and applied voltages, application times, etc. for measuring the glucose, or a calibration curve and a calibration table that have been previously prepared from the ambient temperature.

A clock 25 is connected to the control portion 19. The control portion 19 makes use of the hour and the time of the clock 25 to perform various control operations.

The control portion 19 further includes a correction portion 26 that corrects the measured blood glucose level with the hematocrit value to improve the measurement accuracy of the blood glucose level.

Figure 4:
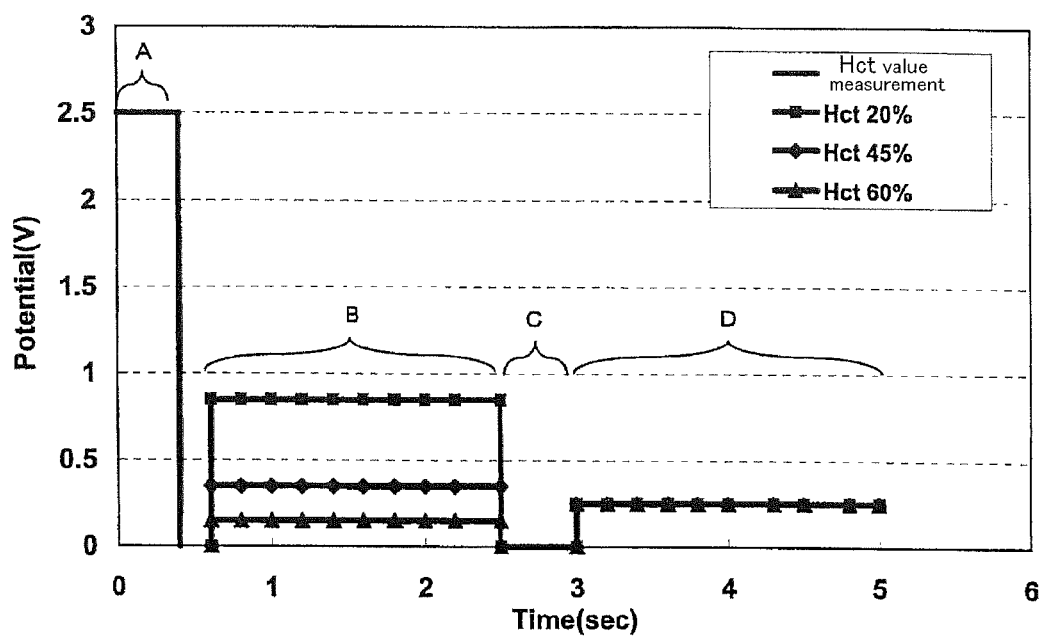
FIG. 4 is a diagram showing the state of a voltage applied over time in a biological information measurement device of an embodiment of the present invention.

One of the characteristics of this embodiment is that the control portion 19 performs a first biological information measurement mode A, a pre-processing application mode B, a voltage application stop mode C, and a second biological information measurement mode D, as shown in FIG. 4. FIG. 4 is a diagram showing the state of a voltage applied over time in a biological information measurement device of an embodiment of the present invention.

In the first biological information measurement mode A of this embodiment, the first biological information (the hematocrit value) is measured based on the current flowing through the first input terminal (not shown) of the input terminal portion 9, i.e., the hematocrit measurement working electrode 5.

In the pre-processing application mode B of this embodiment, a voltage is applied to the second input terminal (not shown) and the third input terminal (not shown) of the input terminal portion 9 in FIG. 1, i.e., the blood component measurement counter electrode 7 and the blood component measurement working electrode 6 after the first biological information measurement mode A.

In the voltage application stop mode C of this embodiment, the application of the voltage to the second input terminal (not shown) and the third input terminal (not shown) of the input terminal portion 9, i.e., the blood component measurement counter electrode 7 and the blood component measurement working electrode 6 is stopped after the pre-processing application mode B.

In the second biological information measurement mode D of this embodiment, the second biological information (the glucose value) is measured by applying a voltage to the second input terminal (not shown) and the third input terminal (not shown) of the input terminal portion 9, i.e., the blood component measurement counter electrode 7 and the blood component measurement working electrode 6 after the voltage application stop mode C.

In this embodiment, the control portion 19 is configured to be able to change the voltage to be applied to the second input terminal (not shown) and the third input terminal (not shown) of the input terminal portion 9, i.e., the blood component measurement counter electrode 7 and the blood component measurement working electrode 6 in the pre-processing application mode B based on the first biological information (the hematocrit value) in the first biological information measurement mode A.

Figure 5:
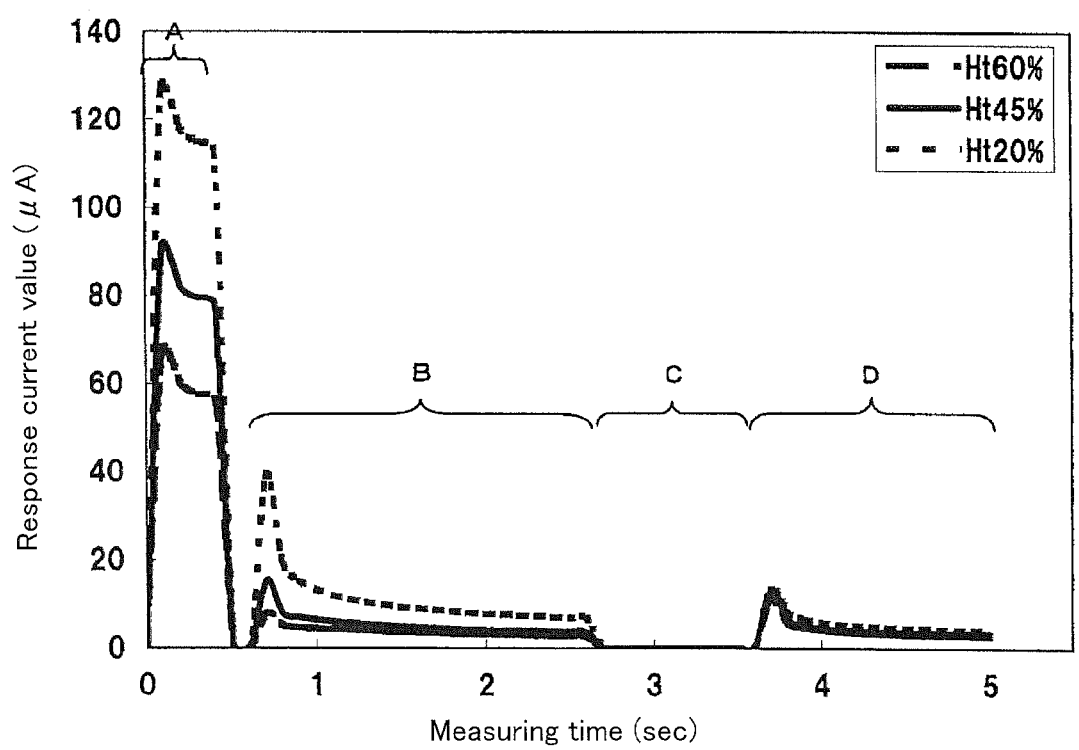
FIG. 5 is a graph showing a change in a response current value (μA) over time in accordance with the application of a voltage in a biological information measurement device of an embodiment of the present invention.

FIG. 5 is a graph showing a change in a response current value (μA) over time in accordance with the application of a voltage in a biological information measurement device of this embodiment. Specifically, FIG. 5 illustrates the properties of the first biological information measurement mode A, the pre-processing application mode B, the voltage application stop mode C, and the second biological information measurement mode D when the hematocrit values (the first biological information) are 20%, 45%, and 60% in the above configuration. FIG. 5 shows the response current value (μA) in each mode. As shown in FIG. 5, the response current value is low when the hematocrit value is high (e.g., 60%), and the response current value is high when the hematocrit value is low (e.g., 20%).

This is because if blood has a high hematocrit value (high Hct value), the viscosity of the blood is increased and the current response is relatively reduced; if blood has a low hematocrit value (low Hct value), the viscosity of the blood is reduced and the current response is relatively increased.

Figure 6:
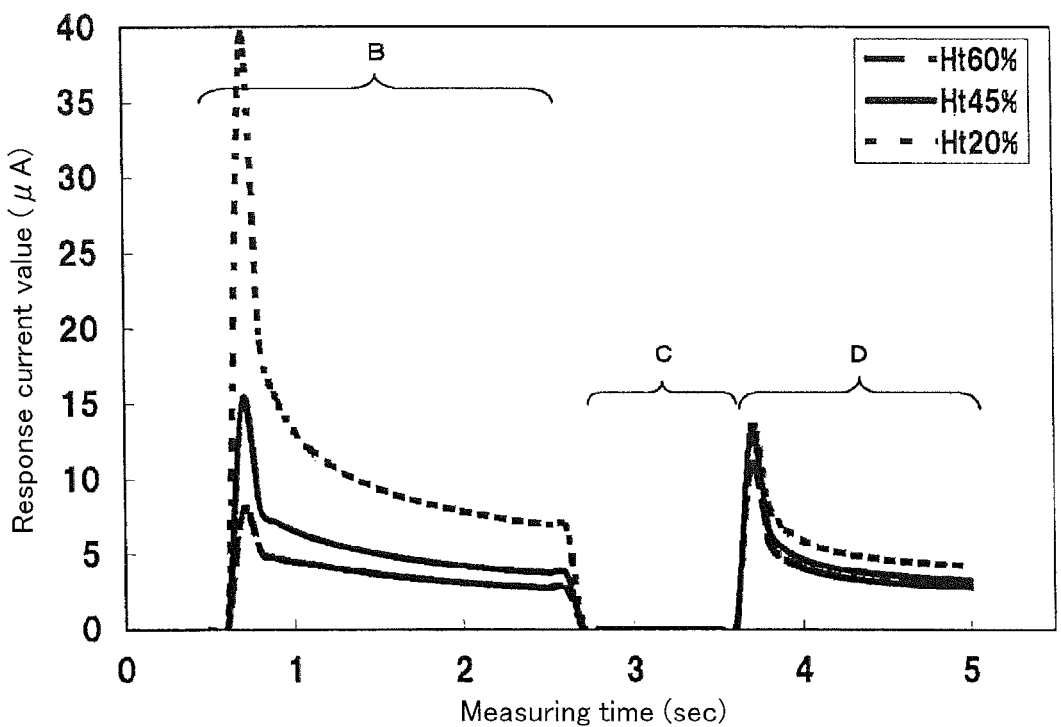
FIG. 6 is a graph showing a change in a response current value (μA) over time in accordance with the application of a voltage in a biological information measurement device of an embodiment of the present invention.

In FIG. 5, it may be difficult to understand the response current changes in the pre-processing application mode B and the second biological information measurement mode D. FIG. 6 is an enlarged view of the response current changes in these modes. As can be sheen from FIG. 6, the pre-processing application mode B and the second biological information measurement mode D also have the properties similar to those of the first biological information measurement mode A. That is, if blood has a high hematocrit value (high Hct value), the viscosity of the blood is increased and the current response is relatively reduced; if blood has a low hematocrit value (low Hct value), the viscosity of the blood is reduced and the current response is relatively increased.

Figure 3:
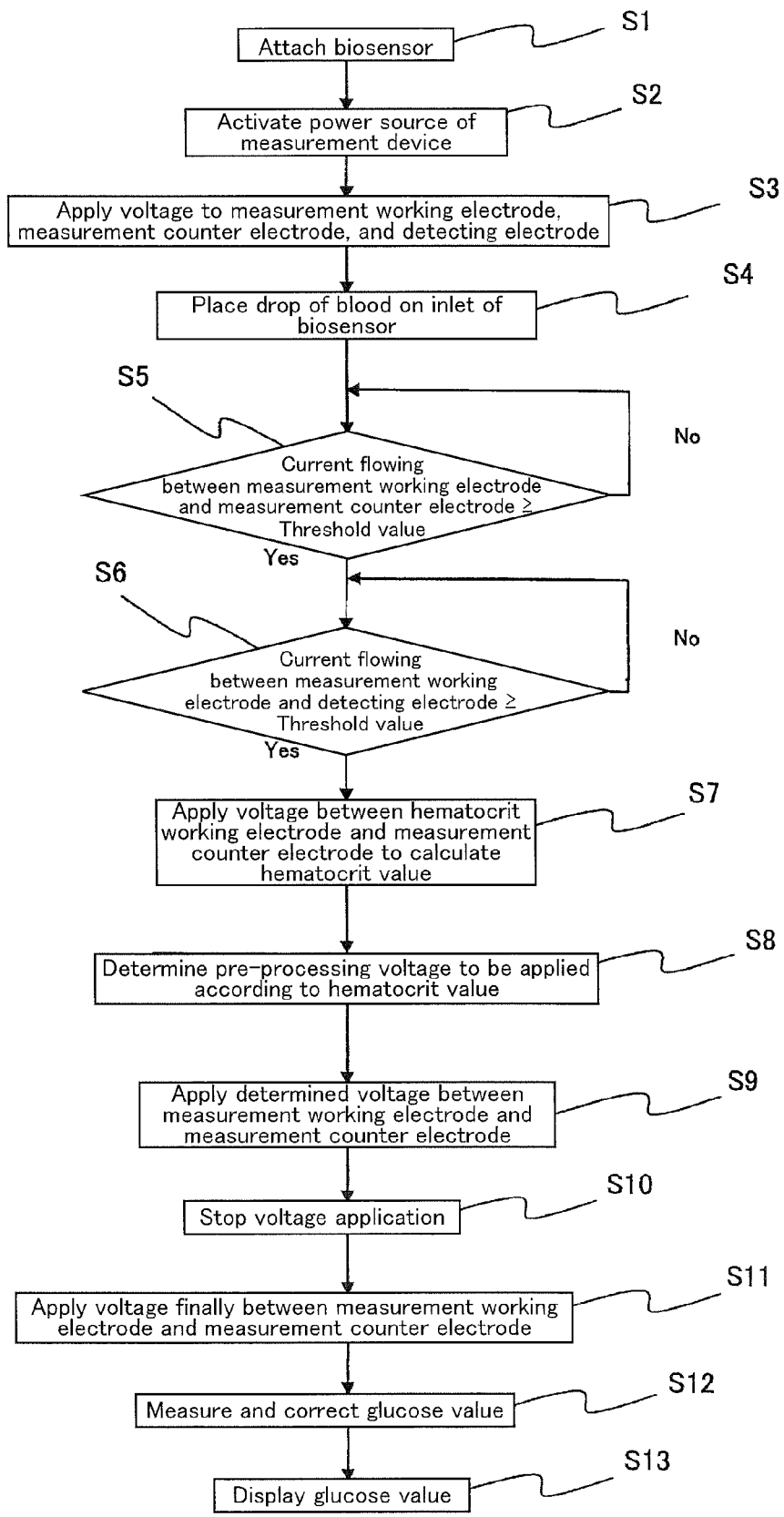
FIG. 3 is an operational flowchart of a biological information measurement device of an embodiment of the present invention.

Next, referring to FIGS. 2 and 3, the measurement flow in the first biological information measurement mode A, the pre-processing application mode B, the voltage application stop mode C, and the second biological information measurement mode D will be described in more detail. FIG. 3 is an operational flowchart of a biological information measurement device of this embodiment.

Before use, a plurality of biosensors 2 (shown in FIG. 2) are stored in a dry container (not shown). The biosensors 2 are taken out of the dry container one by one every time the glucose value (i.e., the blood glucose level or the second biological information) is measured. Then, as shown in FIG. 1, one end of the biosensor 2 is inserted into the insertion port 3 (S1: "Attach biosensor" in FIG. 3) and electrically connected to the input terminal portion 9. Consequently, the control portion 19 recognizes that the biosensor 2 has been attached to the input terminal portion 9, and starts a measuring operation (S2: "Activate power source of measurement device" in FIG. 3).

In this state, a drop of blood of a user has not been placed on the blood inlet 15 yet.

With the start of the measuring operation, the control portion 19 allows an applied voltage to be supplied to each of the blood component measurement working electrode 6, the blood component measurement counter electrode 7, and the blood component introduction detecting electrode 8 of the biosensor 2 via the voltage application portion 17 and the input terminal portion 9 (S3: "Apply voltage to measurement working electrode, measurement counter electrode, and detecting electrode" in FIG. 3).

In this embodiment, the applied voltage supplied to each of the blood component measurement working electrode 6, the blood component measurement counter electrode 7, and the blood component introduction detecting electrode 8 is, e.g., 0.5 V.

Next, a user pricks their finger or the like with a lancet to draw blood and places a drop of blood on the blood inlet 15 of the biosensor 2 (S4: "Place drop of blood on inlet of biosensor" in FIG. 3).

Then, a current begins to flow between the blood component measurement working electrode 6 and the blood component measurement counter electrode 7 and between the blood component measurement working electrode 6 and the blood component introduction detecting electrode 8. This current is converted to a voltage by the current-voltage converter 18, and subsequently the voltage is converted to a digital value by the A/D converter 20. Thereafter, the determination portion 21 of the control portion 19 makes a determination.

Specifically, the control portion 19 measures a value of the current flowing between the blood component measurement working electrode 6 and the blood component measurement counter electrode 7, and compares a voltage value that is proportional to the current value with a predetermined threshold value (e.g., 10 mV). If the voltage value is not less than the threshold value, then the control portion 19 measures a value of the current flowing between the blood component measurement working electrode 6 and the blood component introduction detecting electrode 8.

If the voltage value that is proportional to the value of the current flowing between the blood component measurement working electrode 6 and the blood component measurement counter electrode 7 is less than the threshold value, the determination portion 21 of the control portion 19 determines that the drop of blood still has not sufficiently permeated the reagent 11, and repeats the above comparison until the value of the current flowing between the blood component measurement working electrode 6 and the blood component measurement counter electrode 7 is not less than the threshold value (S5: "Current flowing between measurement working electrode and measurement counter electrode≥Threshold value" in FIG. 3).

Similarly, the control portion 19 measures a value of the current flowing between the blood component measurement working electrode 6 and the blood component introduction detecting electrode 8, compares a voltage value that is proportional to the current value with a predetermined threshold value (e.g., 10 mV), and determines whether the voltage value is not less than the threshold value. If the current value is less than the threshold value, it is determined that the drop of blood still has not sufficiently permeated the reagent 11 and the blood component introduction detecting electrode 8, and the above comparison is repeated until the current value is not less than the threshold value (S6: "Current flowing between measurement working electrode and detecting electrode≥Threshold value" in FIG. 3).

Then, if the current value is not less than the threshold value in the step S5 and the following step S6 in FIG. 3, the determination portion 21 of the control portion 19 determines that the amount of the blood that has been introduced is large enough to be measured.

Next, when it is determined that the amount of the blood that has been introduced is large enough to be measured, the control portion 19 applies, e.g., a voltage of 1.0 to 3.0 V (the applied voltage is 2.5 V in this embodiment) between the hematocrit measurement working electrode 5 and the blood component measurement counter electrode 7 for an application time of 0.01 to 3.0 seconds (the application time is 0.5 seconds in this embodiment) in the first biological information measurement mode A (S7: "Apply voltage between hematocrit working electrode and measurement counter electrode to calculate hematocrit value" in FIG. 3).

As can be seen from FIG. 2, there is a certain space (e.g., 0.01 mm to 10 mm) between the hematocrit measurement working electrode 5 and the blood component measurement counter electrode 7, and no reagent such as an electron carrier is present in this space.

Therefore, an oxidation current that depends on the hematocrit value (the first biological information) can be detected without the influence of the reagent 11 between the hematocrit measurement working electrode 5 and the blood component measurement counter electrode 7.

The oxidation current is recognized as a voltage value by the control portion 19 via the current-voltage converter 18 and the A/D converter 20.

One of the characteristics of this embodiment is that the voltage to be applied in the pre-processing application mode B can be changed based on the oxidation current (which has been converted to a voltage value) that depends on the hematocrit value (the first biological information) and is recognized by the control portion 19.

Specifically, in this embodiment, the voltage to be applied in the pre-processing application mode B can be determined according to the oxidation current (which has been converted to a voltage value) that depends on the detected hematocrit value (the first biological information), using a management table containing hematocrit values (the first biological information) and applied voltages, application times, etc. for measuring the glucose, which has been previously stored in the memory 24.

In other words, if blood has a high hematocrit value (high Hct value), the viscosity of the blood is increased and the current response is relatively reduced during the measurement of the glucose. Therefore, the high-Hct blood requires a voltage to achieve a high current response. If blood has a low hematocrit value (low Hct value), the viscosity of the blood is reduced and the current response is relatively increased during the measurement of the glucose. Therefore, the low-Hct blood requires a voltage to achieve a low current response.

In this embodiment, e.g., the memory 24 stores settings of 0.75 V for a hematocrit value (the first biological information) of 20%, 0.35 V for a hematocrit value of 45%, and 0.15 V for a hematocrit value of 60%. The control portion 19 appropriately selects the voltage to be applied according to these hematocrit values (S8: "Determine pre-processing voltage to be applied according to hematocrit value" in FIG. 3). In this embodiment, the voltage to be applied according to the above hematocrit values may be modified by the ambient temperature. The ambient temperature can be measured by a conventionally known method for measuring the ambient temperature, which will be described later. Such a modification is made because the reaction between the glucose in the blood and the oxidoreductase is an enzyme reaction that is affected by the ambient temperature. Similarly, the predetermined time during which a voltage is applied may also be modified by the ambient temperature.

In this embodiment, when the hematocrit value (the first biological information) represents a first hematocrit value in the memory 24, a first voltage is applied to the second input terminal and the third input terminal in the pre-processing application mode, and when the hematocrit value represents a second hematocrit value in the memory 24, a second voltage is applied to the second input terminal and the third input terminal in the pre-processing application mode. The first hematocrit value may be selected to be larger than the second hematocrit value, and the first voltage may be selected to be smaller than the second voltage.

Alternatively, in this embodiment, when the hematocrit value (the first biological information) represents a first hematocrit value in the memory 24, a first voltage is applied to the second input terminal and the third input terminal in the pre-processing application mode, when the hematocrit value represents a second hematocrit value in the memory 24, a second voltage is applied to the second input terminal and the third input terminal in the pre-processing application mode, and when the hematocrit value represents a third hematocrit value in the memory 24, a third voltage is applied to the second input terminal and the third input terminal in the pre-processing application mode. The first hematocrit value may be selected to be larger than the second hematocrit value and the third hematocrit value, and the second hematocrit value may be selected to be larger than the third hematocrit value. The first voltage may be selected to be smaller than the second voltage and the third voltage, and the second voltage may be selected to be smaller than the third voltage.

Next, in this embodiment, the control portion 19 applies the voltage that has been determined according to the measured hematocrit value (the first biological information) between the blood component measurement working electrode 6 and the blood component measurement counter electrode 7, e.g., for a predetermined time of 0.5 to 4.0 seconds (for 2.0 seconds in this embodiment) in the pre-processing application mode B (S9: "Apply determined voltage between measurement working electrode and measurement counter electrode" in FIG. 3).

Thereafter, in this embodiment, the control portion 19 stops the application of the voltage to all the electrodes (the hematocrit measurement working electrode 5, the blood component measurement working electrode 6, the blood component measurement counter electrode 7, and the blood component introduction detecting electrode 8) of the biosensor 2 for about 0.1 to 5.0 seconds (for 1.0 second in this embodiment) in order to further accelerate the reaction between the glucose in the blood and the reagent 11 containing the oxidoreductase and the electron carrier in the voltage application stop mode C (S10: "Stop voltage application" in FIG. 3).

Then, in the voltage application stop mode C, the glucose in the blood reacts with the oxidoreductase for a certain period of time.

In the next second biological information measurement mode D, the control portion 19 applies a voltage between the blood component measurement working electrode 6 and the blood component measurement counter electrode 7, oxidizes the reduced electron carrier that is generated on the blood component measurement working electrode 6 by the enzyme reaction, and detects the oxidation current, thereby measuring a glucose (blood glucose) value (the second biological information).

The reaction time between the glucose and the oxidoreductase in the second biological information measurement mode D is, e.g., 0.5 to 20 seconds, and more preferably 0.5 to 10 seconds. In this embodiment, a voltage of 0.05 to 1.0 V, and more preferably a voltage of 0.1 to 0.8 V (0.25 V in this embodiment) is applied between the blood component measurement working electrode 6 and the blood component measurement counter electrode 7 for 1.5 seconds.

In this embodiment, the control portion 19 calculates the glucose value (the second biological information) after an application time of 1.5 seconds has elapsed (S11: "Apply voltage finally between measurement working electrode and measurement counter electrode" in FIG. 3).

In this embodiment, the calculated glucose value (the second biological information) is subjected to a conventionally known temperature correction (S12: "Measure and correct glucose value" in FIG. 3).

The temperature correction is performed because the enzyme reaction for measuring the glucose value is affected by the ambient temperature. However, in the step S8 of determining a pre-processing voltage to be applied according to the hematocrit value, as shown in FIG. 3, if the voltage to be applied and/or the application time according to the hematocrit value are modified by the ambient temperature, the glucose value may be either corrected or not corrected at this stage. On the other hand, in the step S8 of determining a pre-processing voltage to be applied according to the hematocrit value, as shown in FIG. 3, if the voltage to be applied and the application time according to the hematocrit value are not modified by the ambient temperature, the glucose value needs to be corrected at this stage.

The glucose value thus corrected is displayed on the display portion 22 as a final glucose (blood glucose) value (the second biological information) (S13: "Display glucose value" in FIG. 3).

One of the characteristics of this embodiment is that the voltage to be applied in the pre-processing application mode B can be changed based on the oxidation current (which has been converted to a voltage value) that depends on the hematocrit value (the first biological information) and is recognized by the control portion 19. Consequently, the blood glucose level displayed on the display portion 22 can achieve extremely high accuracy.

Hereinafter, this point will be described with reference to FIGS. 7 to 14.

Figure 7:
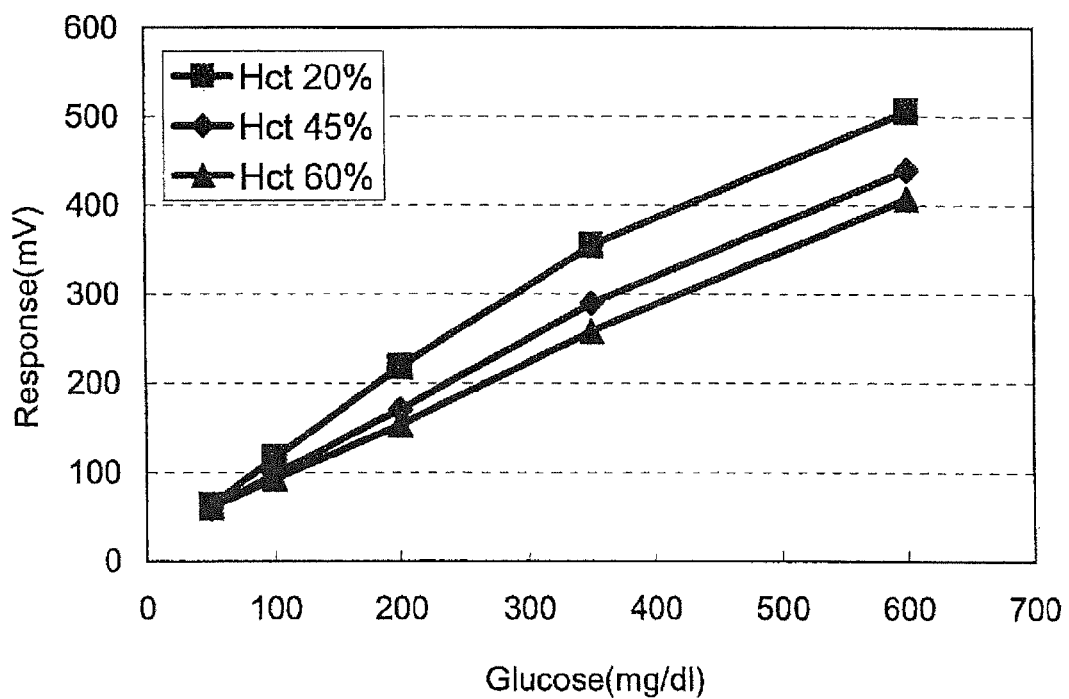
FIG. 7 is a graph showing a change in an output voltage (mV) with a blood glucose level in a biological information measurement device of an embodiment of the present invention.

FIG. 7 is a graph showing a change in an output voltage (mV) with a blood glucose level in a biological information measurement device of an embodiment of the present invention. Specifically, in this embodiment, FIG. 7 illustrates how the output of the A/D converter 20 (FIG. 1) is changed with the blood glucose level in the second biological information measurement mode D when the hematocrit values are 20%, 45%, and 60% (corresponding to the state before the correction in the step S12 in FIG. 3). As can be seen from FIG. 7, the output voltage increases with increasing the blood glucose level no matter whether the hematocrit value is 20%, 45%, or 60%.

Figure 11:
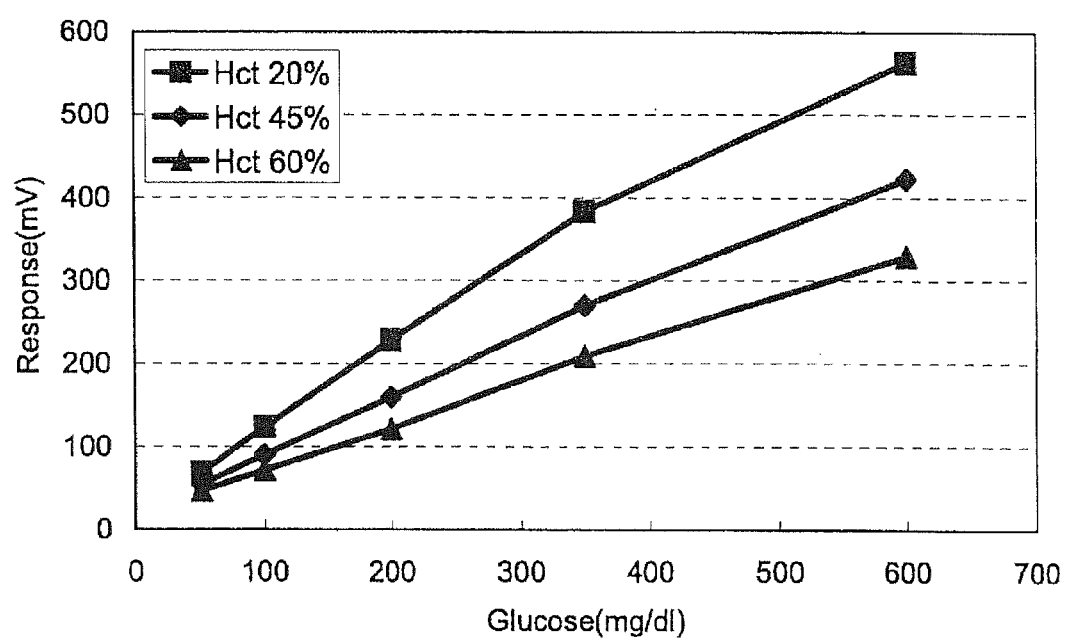
FIG. 11 is a graph showing a change in an output voltage (mV) with a blood glucose level in a biological information measurement device of a conventional example.

On the other hand, FIG. 11 is a graph showing a change in an output voltage (mV) with a blood glucose level in a biological information measurement device of a conventional example. Specifically, in the conventional example, FIG. 11 illustrates how the output of the A/D converter 20 (FIG. 1) is changed with the blood glucose level in the second biological information measurement mode D when the hematocrit values are 20%, 45%, and 60%. As can be seen from FIG. 11, similarly to FIG. 7, the output voltage increases with increasing the blood glucose level no matter whether the hematocrit value is 20%, 45%, or 60%.

Comparing FIG. 7 (this embodiment) and FIG. 11 (the conventional example) shows that a variation in the detected blood glucose level (the second biological information) is small even if the hematocrit values (the first biological information) differ in this embodiment. For example, in FIG. 11 (the conventional example), when the blood glucose level is 350 mg/dl, the output voltage is 280 mV for a hematocrit value of 45%, but the output voltage is increased to 390 mV for a hematocrit value of 20%, resulting in a difference of 110 mV.

Moreover, in FIG. 11 (the conventional example), while the output voltage is 280 mV for a hematocrit value of 45%, the output voltage is reduced to 200 mV for a hematocrit value of 60%, resulting in a difference of 80 mV.

On the other hand, in FIG. 7 (this embodiment), when the blood glucose level is 350 mg/dl, the output voltage is 290 mV for a hematocrit value of 45%, and the output voltage is 360 mV for a hematocrit value of 20%, making only a difference of 70 mV.

Moreover, in FIG. 7 (this embodiment), while the output voltage is 290 mV for a hematocrit value of 45%, the output voltage is 250 mV for a hematocrit value of 60%, making only a difference of 40 mV.

As a result of changing the voltage to be applied between the blood component measurement working electrode 6 and the blood component measurement counter electrode 7 in the pre-processing application mode B, as shown in FIG. 4, this embodiment can reduce a difference in the output voltage between the hematocrit values.

In other words, this embodiment deals with the following points. As described above, if blood has a high hematocrit value (high Hct value), the viscosity of the blood is increased and the current response is relatively reduced during the measurement of the glucose. Therefore, the high-Hct blood requires a voltage to achieve a high current response. If blood has a low hematocrit value (low Hct value), the viscosity of the blood is reduced and the current response is relatively increased during the measurement of the glucose. Therefore, the low-Hct blood requires a voltage to achieve a low current response.

In contrast, the conventional example applies the same voltage between the blood component measurement working electrode 6 and the blood component measurement counter electrode 7 in the pre-processing application mode B regardless of the hematocrit value (FIG. 11), so that the output voltage varies greatly. FIG. 11 is a graph showing a change in an output voltage (mV) with a blood glucose level in a biological information measurement device of the conventional example.

Figure 12:
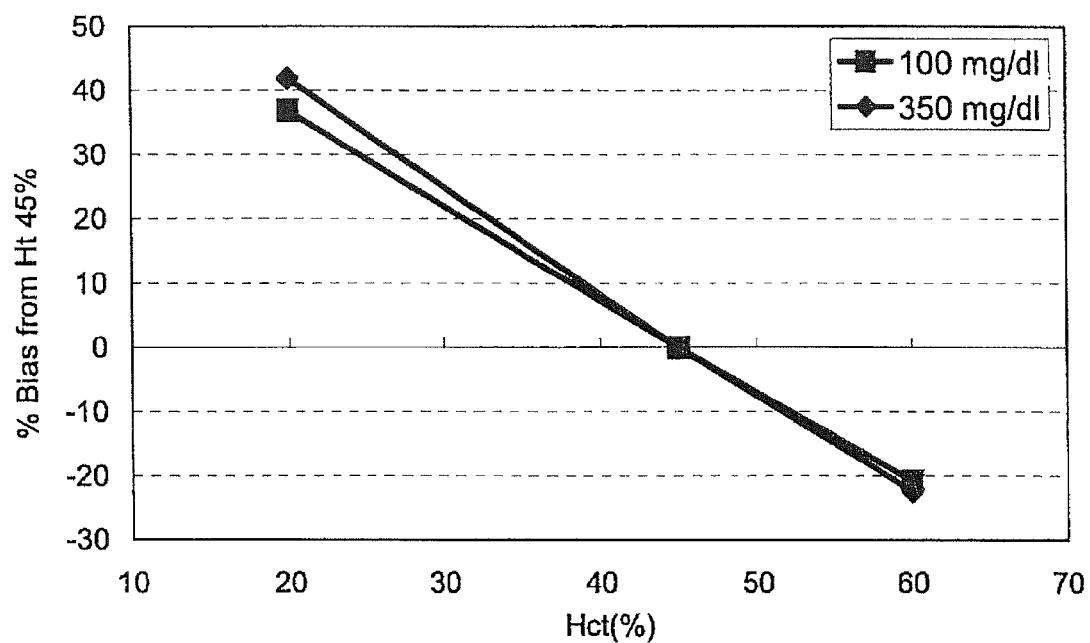
FIG. 12 is a graph showing a difference in sensitivity of an output voltage (mV) with respect to a hematocrit value in a biological information measurement device of a conventional example.

FIG. 12 is a graph showing a difference in sensitivity of an output voltage (mV) with respect to a hematocrit value in a biological information measurement device of the conventional example. Specifically, FIG. 12 illustrates a difference (the degree of influence) in each of the samples with blood glucose levels of 100 mg/111 and 350 mg/dl when their hematocrit values are 20% and 60% as compared to 45% in the conventional example.

FIG. 12 (the conventional example) shows that both the samples with blood glucose levels of 100 mg/dl and 350 mg/dl have a difference of 35% or more on the hematocrit 20% side and a difference of 20% or more on the hematocrit 60% side from the hematocrit value 45%.

Thus, in the conventional example, the output voltage of the A/D converter 20 varies greatly depending on the hematocrit value, as can be seen from FIGS. 11 and 12.

The conventional example also has made an attempt to calculate the final blood glucose level by correcting the output voltage of the A/D converter 20 in accordance with the subsequently detected hematocrit value.

Figure 13:
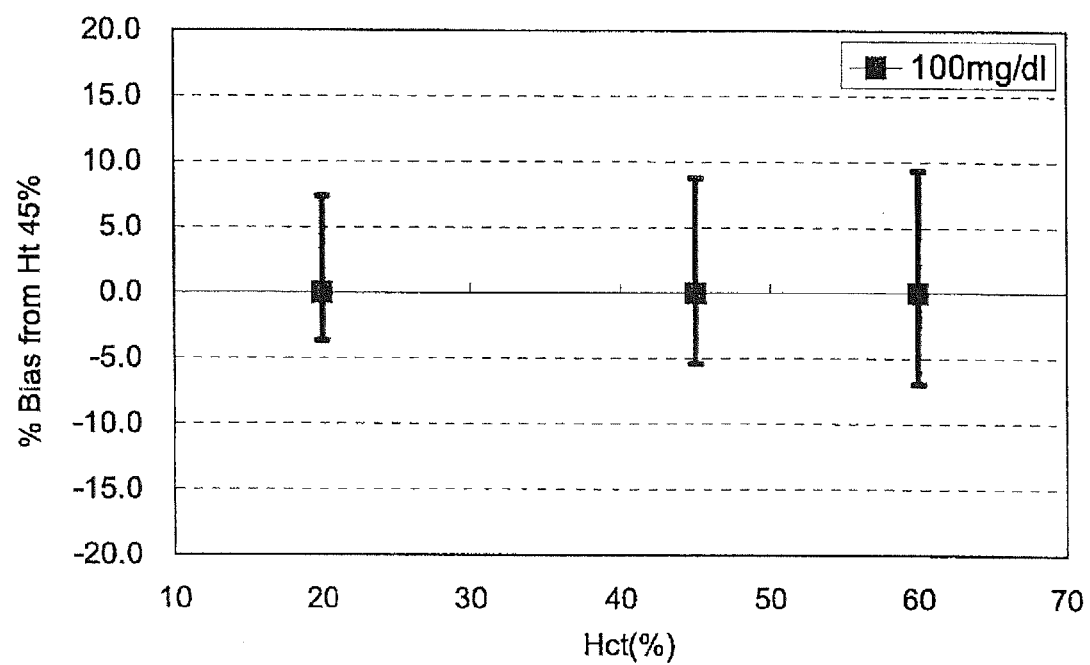
FIG. 13 is a graph showing a difference in sensitivity of an output voltage (mV) with respect to a hematocrit value in a biological information measurement device of a conventional example.

However, in this conventional example, as shown in FIG. 13, the sample with a blood glucose level of 100 mg/dl has a variation of +7.5% to −4.0% when the hematocrit value is 20%, a variation of +9.0% to −5.0% when the hematocrit value is 45%, and a variation of +9.5% to −7.0% when the hematocrit value is 60%. FIG. 13 is a graph showing a difference in sensitivity of an output voltage (mV) with respect to a hematocrit value in a biological information measurement device of the conventional example.

Figure 14:
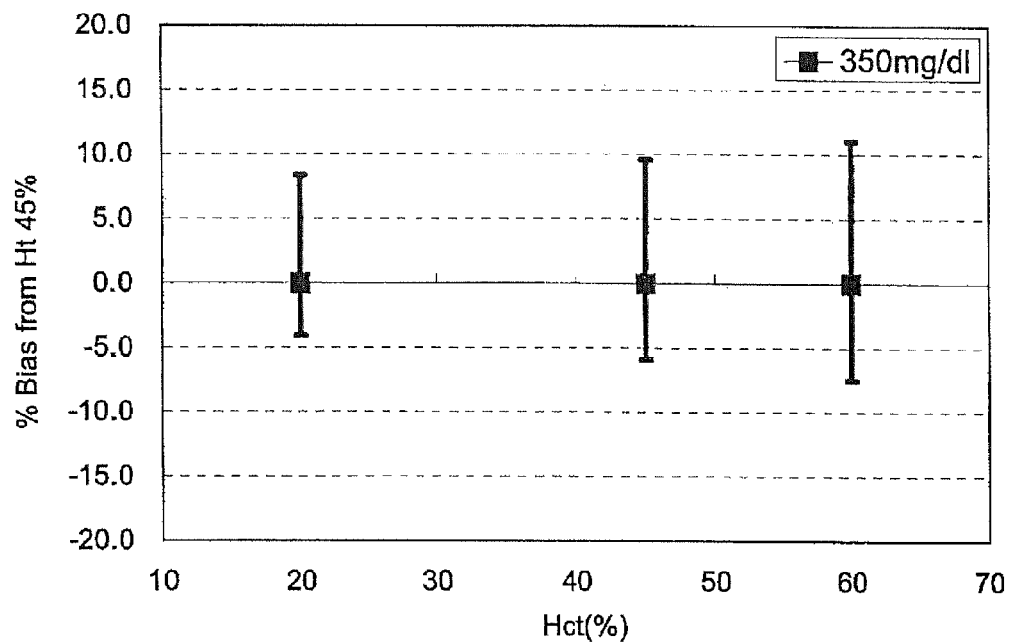
FIG. 14 is a graph showing a difference in sensitivity of an output voltage (mV) with respect to a hematocrit value in a biological information measurement device of a conventional example.

As shown in FIG. 14, the sample with a blood glucose level of 350 mg/dl has a variation of +8.0% to −4.0% when the hematocrit value is 20%, a variation of +10.0% to −6.0% when the hematocrit value is 45%, and a variation of +11.0% to −7.5% when the hematocrit value is 60%. FIG. 14 is a graph showing a difference in sensitivity of an output voltage (mV) with respect to a hematocrit value in a biological information measurement device of the conventional example.

Even if subsequent corrections are performed while there is such a great variation, the final blood glucose level will still vary significantly.

Thus, the measurement accuracy is low in the conventional biological information measurement device.

Figure 8:
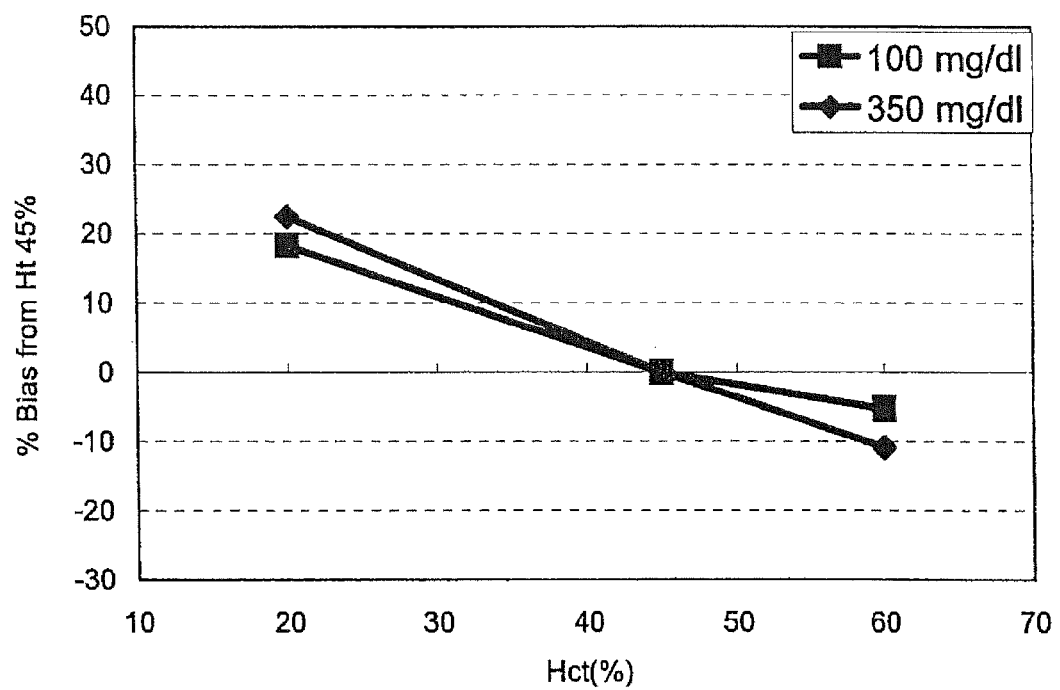
FIG. 8 is a graph showing a difference in sensitivity of an output voltage (mV) with respect to a hematocrit value in a biological information measurement device of an embodiment of the present invention.

Contrary to the conventional example, FIG. 8 is a graph showing a difference in sensitivity of an output voltage (mV) with respect to a hematocrit value in a biological information measurement device of this embodiment. Specifically, FIG. 8 illustrates a difference (the degree of influence) in each of the samples with blood glucose levels of 100 mg/dl and 350 mg/dl when their hematocrit values are 20% and 60% as compared to 45% in this embodiment.

FIG. 8 (this embodiment) shows that both the samples with blood glucose levels of 100 mg/dl and 350 mg/dl have only a difference of about 20% on the hematocrit 20% side and only a difference of about 10% on the hematocrit 60% side from the hematocrit value 45%.

Thus, in this embodiment, the output voltage of the A/D converter 20 varies slightly depending on the hematocrit value, as can be seen from FIGS. 7 and 8.

Therefore, this embodiment shows only a small variation when the final blood glucose level is calculated from the output voltage of the A/D converter 20.

Figure 9:
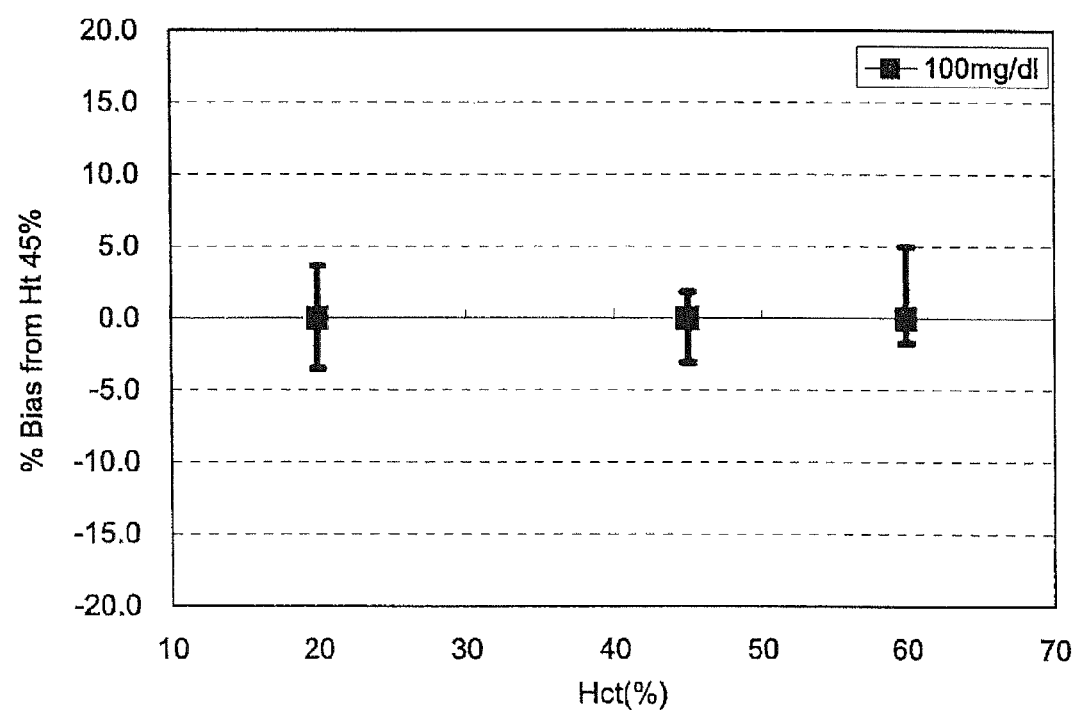
FIG. 9 is a graph showing a difference in sensitivity of an output voltage (mV) with respect to a hematocrit value in a biological information measurement device of an embodiment of the present invention.
Figure 10:
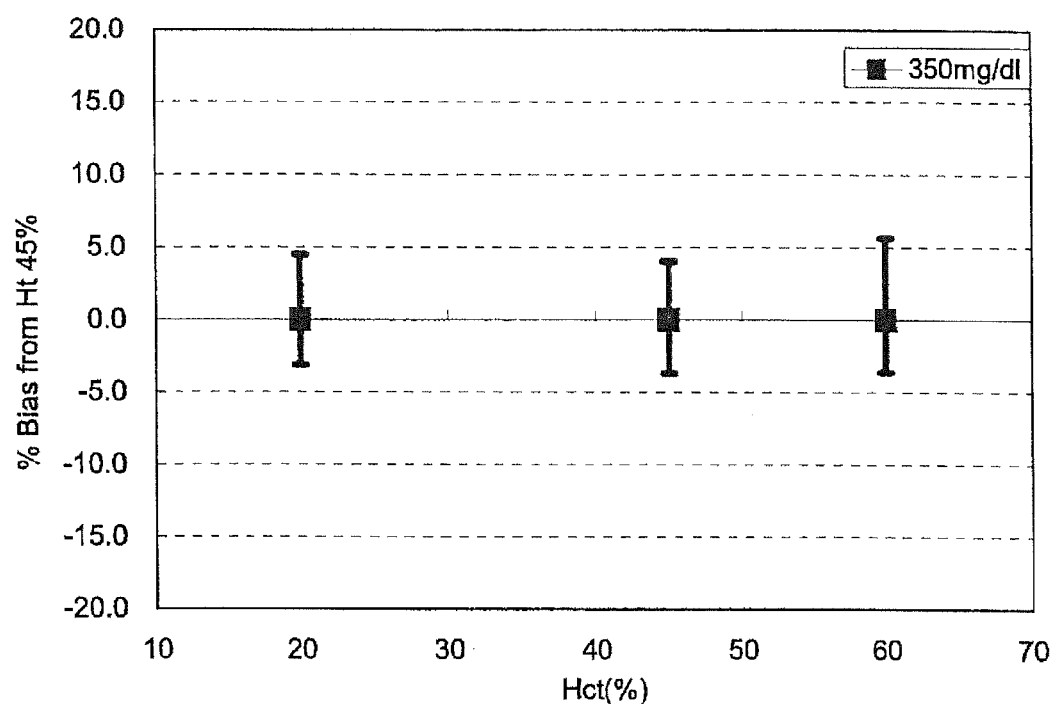
FIG. 10 is a graph showing a difference in sensitivity of an output voltage (mV) with respect to a hematocrit value in a biological information measurement device of an embodiment of the present invention.

This point will be further described with reference to FIGS. 9 and 10. FIGS. 9 and 10 are graphs showing a difference in sensitivity of an output voltage (mV) with respect to a hematocrit value in a biological information measurement device of this embodiment. As shown in FIG. 9, the sample with a blood glucose level of 100 mg/dl has only a variation of +3.0% to −3.0% when the hematocrit value is 20%, only a variation of +2.0% to −3.0% when the hematocrit value is 45%, and only a variation of +5.0% to −2.0% when the hematocrit value is 60%.

As shown in FIG. 10, the sample with a blood glucose level of 350 mg/dl has only a variation of +4.5% to −3.0% when the hematocrit value is 20%, only a variation of +4.0% to −4.0% when the hematocrit value is 45%, and only a variation of +6.0% to −4.0% when the hematocrit value is 60%.

Therefore, in this embodiment, since the blood glucose level itself is measured under the conditions that are not much affected by the hematocrit value, the measurement accuracy can be improved.

This embodiment performs a temperature correction in the step S12 in FIG. 3 in order to reduce the influence of the temperature, so that the measurement accuracy can be improved further.

In this embodiment, if the resultant hematocrit value (the first biological information) is a standard value (e.g., the hematocrit value is 42), it is not necessary to change the voltage to be applied in the pre-processing application mode B and the voltage application time during which a voltage is applied between the blood component measurement counter electrode 7 and the blood component measurement working electrode 6 in the second biological information measurement mode D.

Embodiment 2

FIGS. 15 to 22 show Embodiment 2 of the present invention. Similarly to Embodiment 1, Embodiment 2 can change a voltage to be applied between the blood component measurement counter electrode 7 and the blood component measurement working electrode 6 in the pre-processing application mode B based on the hematocrit value (the first biological information) measured in the first biological information measurement mode A. Moreover, Embodiment 2 can change a voltage application time during which a voltage is applied between the blood component measurement counter electrode 7 and the blood component measurement working electrode 6 in the second biological information measurement mode D based on the first biological information (the hematocrit value) in the first biological information measurement mode A.

Figure 15:
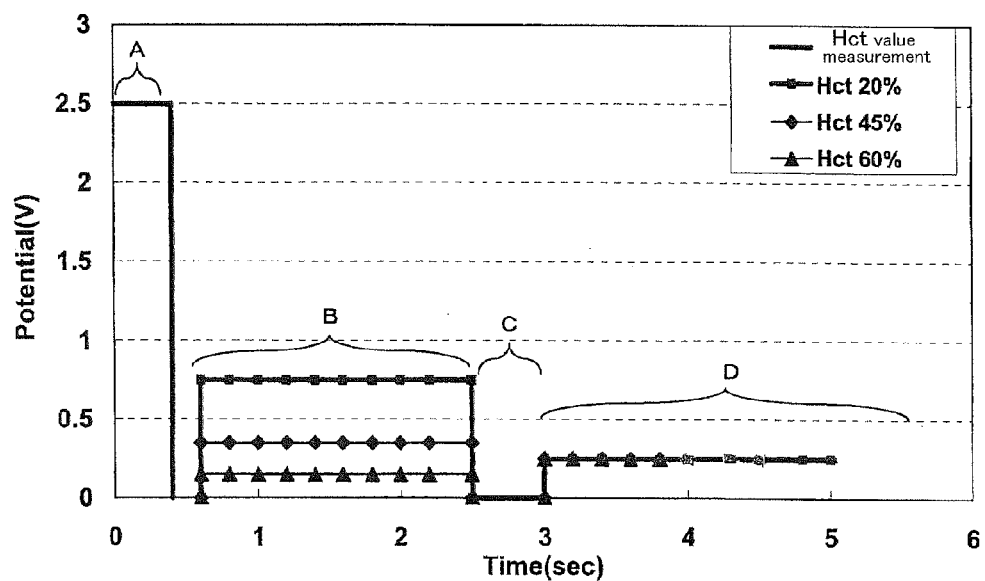
FIG. 15 is a diagram showing the state of a voltage applied over time in a biological information measurement device of another embodiment of the present invention.

FIG. 15 is a diagram showing the state of a voltage applied over time in a biological information measurement device of this embodiment. In the first biological information measurement mode A of FIG. 15, the first biological information (the hematocrit value) is measured based on the current flowing through the first input terminal (not shown) of the input terminal portion 9, i.e., the hematocrit measurement working electrode 5.

In the pre-processing application mode B of this embodiment, a voltage is applied to the second input terminal (not shown) and the third input terminal (not shown) of the input terminal portion 9 in FIG. 1, i.e., the blood component measurement counter electrode 7 and the blood component measurement working electrode 6 after the first biological information measurement mode A.

In the voltage application stop mode C of this embodiment, the application of the voltage to the second input terminal (not shown) and the third input terminal (not shown) of the input terminal portion 9, i.e., the blood component measurement counter electrode 7 and the blood component measurement working electrode 6 is stopped after the pre-processing application mode B.

In the second biological information measurement mode D of this embodiment, the second biological information (the glucose value) is measured by applying a voltage to the second input terminal (not shown) and the third input terminal (not shown) of the input terminal portion 9, i.e., the blood component measurement counter electrode 7 and the blood component measurement working electrode 6 after the voltage application stop mode C.

In this embodiment, the control portion 19 is configured to be able to change the voltage to be applied to the second input terminal (not shown) and the third input terminal (not shown) of the input terminal portion 9, i.e., the blood component measurement counter electrode 7 and the blood component measurement working electrode 6 in the pre-processing application mode B based on the first biological information (the hematocrit value) in the first biological information measurement mode A.

Figure 16:
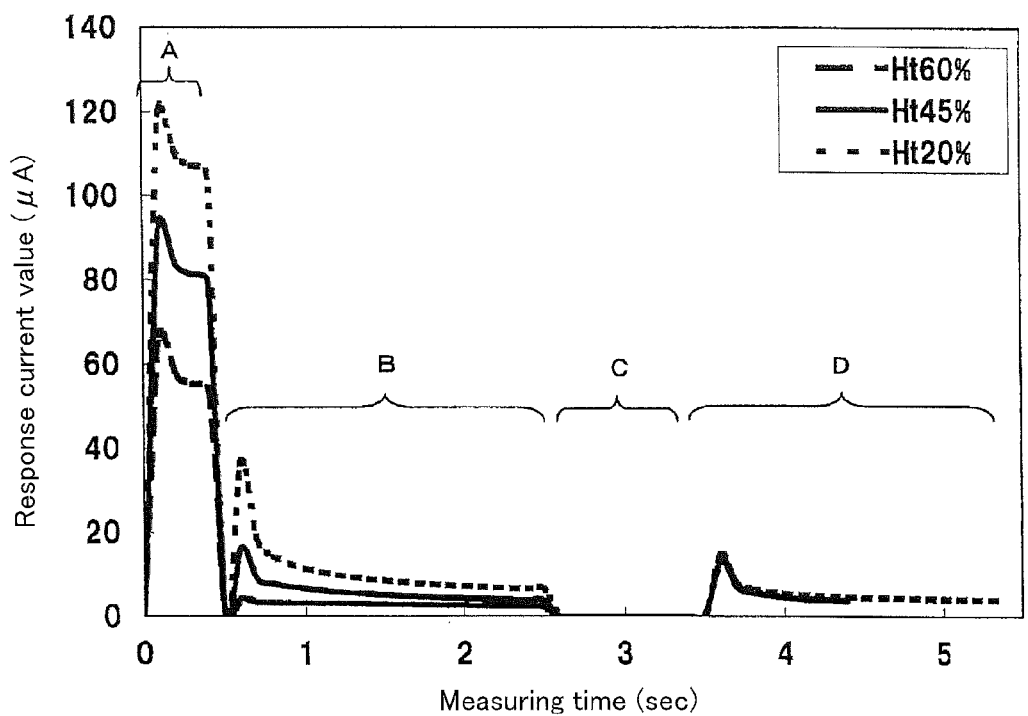
FIG. 16 is a graph showing a change in a response current value (μA) over time in accordance with the application of a voltage in a biological information measurement device of another embodiment of the present invention.

FIG. 16 is a graph showing a change in a response current value (μA) over time in accordance with the application of a voltage in a biological information measurement device of another embodiment of the present invention. Specifically, FIG. 16 illustrates the properties of the first biological information measurement mode A, the pre-processing application mode B, the voltage application stop mode C, and the second biological information measurement mode D when the hematocrit values are 20%, 45%, and 60% in the above configuration. FIG. 16 shows the response current value (μA) in each mode. As shown in FIG. 16, the response current value is low when the hematocrit value is high (e.g., 60%), and the response current value is high when the hematocrit value is low (e.g., 20%).

This is because if blood has a high hematocrit value (high Hct value), the viscosity of the blood is increased and the current response is relatively reduced; if blood has a low hematocrit value (low Hct value), the viscosity of the blood is reduced and the current response is relatively increased.

Figure 17:
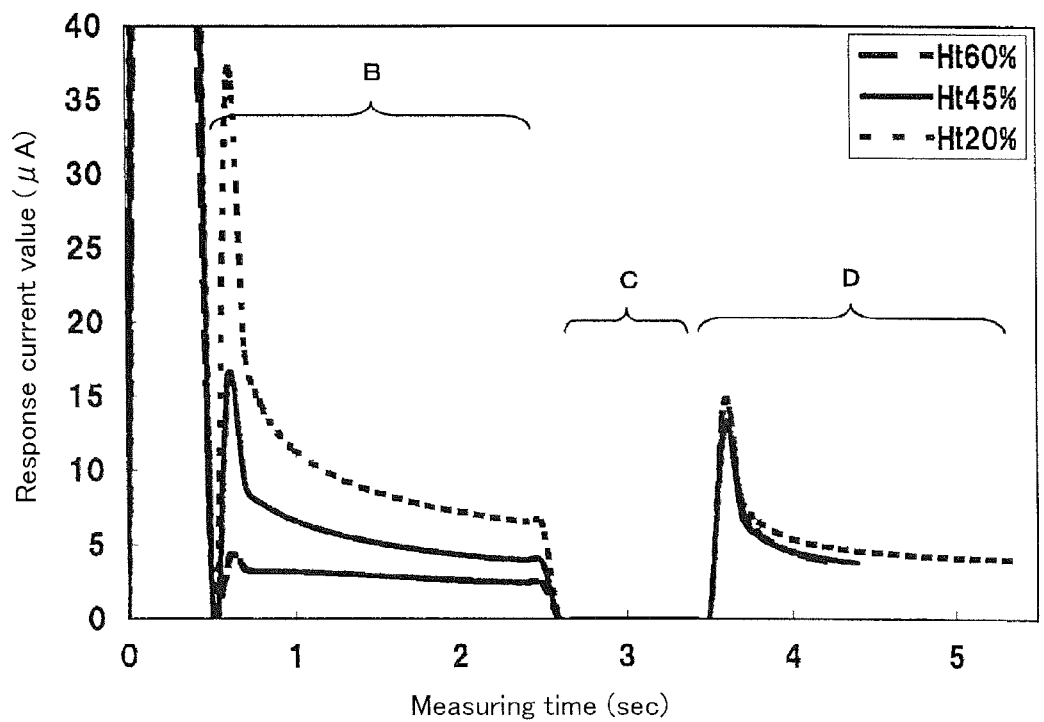
FIG. 17 is a graph showing a change in a response current value (μA) over time in accordance with the application of a voltage in a biological information measurement device of another embodiment of the present invention.

In FIG. 16, it may be difficult to understand the response current changes in the pre-processing application mode B and the second biological information measurement mode D. FIG. 17 is an enlarged view of the response current changes in these modes. As can be seen from FIG. 17, the pre-processing application mode B and the second biological information measurement mode D also have the properties similar to those of the first biological information measurement mode A. That is, if blood has a high hematocrit value (high Hct value), the viscosity of the blood is increased and the current response is relatively reduced; if blood has a low hematocrit value (low Hct value), the viscosity of the blood is reduced and the current response is relatively increased.

Figure 22:
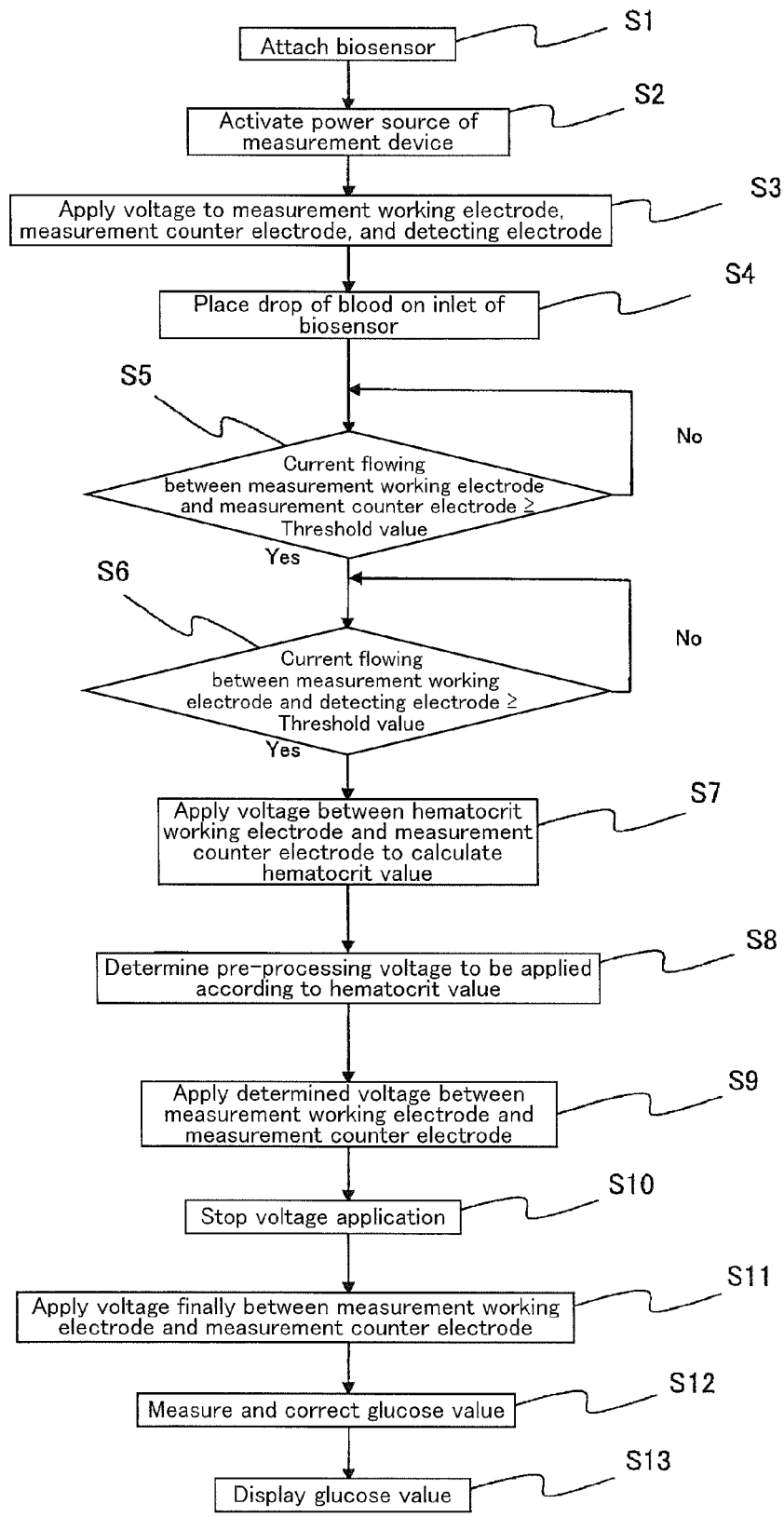
FIG. 22 is an operational flowchart of a biological information measurement device of another embodiment of the present invention.

Next, referring to FIGS. 2 and 22, the measurement flow in the first biological information measurement mode A, the pre-processing application mode B, the voltage application stop mode C, and the second biological information measurement mode D will be described in more detail. FIG. 22 is an operational flowchart of a biological information measurement device of this embodiment.

Before use, a plurality of biosensors 2 (shown in FIG. 2) are stored in a dry container (not shown). The biosensors 2 are taken out of the dry container one by one every time the glucose value (i.e., the blood glucose level or the second biological information) is measured. Then, as shown in FIG. 1, one end of the biosensor 2 is inserted into the insertion port 3 (S1; "Attach biosensor" in FIG. 22) and electrically connected to the input terminal portion 9. Consequently, the control portion 19 recognizes that the biosensor 2 has been attached to the input terminal portion 9, and starts a measuring operation (S2; "Activate power source of measurement device" in FIG. 22).

In this state, a drop of blood of a user has not been placed on the blood inlet 15 yet.

With the start of the measuring operation, the control portion 19 allows an applied voltage to be supplied to each of the blood component measurement working electrode 6, the blood component measurement counter electrode 7, and the blood component introduction detecting electrode 8 of the biosensor 2 via the voltage application portion 17 and the input terminal portion 9 (S3; "Apply voltage to measurement working electrode, measurement counter electrode, and detecting electrode" in FIG. 22).

In this embodiment, the applied voltage supplied to each of the blood component measurement working electrode 6, the blood component measurement counter electrode 7, and the blood component introduction detecting electrode 8 is, e.g., 0.5 V.

Next, a user pricks their finger or the like with a lancet to draw blood and places a drop of blood on the blood inlet 15 of the biosensor 2 (S4: "Place drop of blood on inlet of biosensor" in FIG. 22).

Then, a current begins to flow between the blood component measurement working electrode 6 and the blood component measurement counter electrode 7 and between the blood component measurement working electrode 6 and the blood component introduction detecting electrode 8. This current is converted to a voltage by the current-voltage converter 18, and subsequently the voltage is converted to a digital value by the A/D converter 20. Thereafter, the determination portion 21 of the control portion 19 makes a determination.

Specifically, the control portion 19 measures a value of the current flowing between the blood component measurement working electrode 6 and the blood component measurement counter electrode 7, and compares a voltage value that is proportional to the current value with a predetermined threshold value (e.g., 10 mV). If the voltage value is not less than the threshold value, then the control portion 19 measures a value of the current flowing between the blood component measurement working electrode 6 and the blood component introduction detecting electrode 8.

If the voltage value that is proportional to the value of the current flowing between the blood component measurement working electrode 6 and the blood component measurement counter electrode 7 is less than the threshold value, the determination portion 21 of the control portion 19 determines that the drop of blood still has not sufficiently permeated the reagent 11, and repeats the above comparison until the value of the current flowing between the blood component measurement working electrode 6 and the blood component measurement counter electrode 7 is not less than the threshold value (S5: "Current flowing between measurement working electrode and measurement counter electrode≥Threshold value" in FIG. 22).

Similarly, the control portion 19 measures a value of the current flowing between the blood component measurement working electrode 6 and the blood component introduction detecting electrode 8, compares a voltage value that is proportional to the current value with a predetermined threshold value (e.g., 10 mV), and determines whether the voltage value is not less than the threshold value. If the value is less than the threshold value, it is determined that the drop of blood still has not sufficiently permeated the reagent 11 and the blood component introduction detecting electrode 8, and the above comparison is repeated until the value is not less than the threshold value (S6: "Current flowing between measurement working electrode and detecting electrode-≥Threshold value" in FIG. 22).

Then, if the current value is not less than the threshold value in the step S5 and the following step S6 in FIG. 22, the determination portion 21 of the control portion 19 determines that the amount of the blood that has been introduced is large enough to be measured.

Next, when it is determined that the amount of the blood that has been introduced is large enough to be measured, the control portion 19 applies, e.g., a voltage of 1.0 to 3.0 V (the applied voltage is 2.5 V in this embodiment) between the hematocrit measurement working electrode 5 and the blood component measurement counter electrode 7 for an application time of 0.01 to 3.0 seconds (the application time is 0.5 seconds in this embodiment) in the first biological information measurement mode A (S7: "Apply voltage between hematocrit working electrode and measurement counter electrode to calculate hematocrit value" in FIG. 22).

As can be seen from FIG. 2, there is a certain space (e.g., 0.01 mm to 10 mm) between the hematocrit measurement working electrode 5 and the blood component measurement counter electrode 7, and no reagent such as an electron carrier is present in this space.

Therefore, only the blood flowing into the space between the hematocrit measurement working electrode 5 and the blood component measurement counter electrode 7 serves as an electron carrier. Consequently, an oxidation current that depends on the hematocrit value (the first biological information) can be detected without the influence of the reagent 11.

The oxidation current is recognized as a voltage value by the control portion 19 via the current-voltage converter 18 and the A/D converter 20.

One of the characteristics of this embodiment is that the voltage to be applied in the pre-processing application mode B and the voltage application time during which a voltage is applied between the blood component measurement counter electrode 7 and the blood component measurement working electrode 6 in the second biological information measurement mode D can be changed based on the oxidation current (which has been converted to a voltage value) that depends on the hematocrit value (the first biological information) and is recognized by the control portion 19.

Specifically, in this embodiment, the voltage to be applied in the pre-processing application mode B can be determined according to the oxidation current (which has been converted to a voltage value) that depends on the detected hematocrit value (the first biological information), using a management table containing hematocrit values (the first biological information) and applied voltages, application times, etc. for measuring the glucose, which has been previously stored in the memory 24.

In other words, if blood has a high hematocrit value (high Hct value), the viscosity of the blood is increased and the current response is relatively reduced during the measurement of the glucose. Therefore, the high-Hct blood requires a voltage to achieve a high current response. If blood has a low hematocrit value (low Hct value), the viscosity of the blood is reduced and the current response is relatively increased during the measurement of the glucose. Therefore, the low-Hct blood requires a voltage to achieve a low current response.

In this embodiment, e.g., the memory 24 stores settings of 0.75 V for a hematocrit value (the first biological information) of 20%, 0.35 V for a hematocrit value of 45%, and 0.15 V for a hematocrit value of 60%. The control portion 19 appropriately selects the voltage to be applied according to these hematocrit values (S8: "Determine pre-processing voltage to be applied and final application time according to hematocrit value" in FIG. 22). In this embodiment, the voltage to be applied according to the above hematocrit values may be modified by the ambient temperature. The ambient temperature can be measured by a conventionally known method for measuring the ambient temperature, which will be described later. Such a modification is made because the reaction between the glucose in the blood and the oxidoreductase is an enzyme reaction that is affected by the ambient temperature. Similarly, the predetermined time during which a voltage is applied may also be modified by the ambient temperature.

In this embodiment, when the hematocrit value (the first biological information) represents a first hematocrit value in the memory 24, a first voltage is applied to the second input terminal and the third input terminal in the pre-processing application mode, and when the hematocrit value represents a second hematocrit value in the memory 24, a second voltage is applied to the second input terminal and the third input terminal in the pre-processing application mode. The first hematocrit value may be selected to be larger than the second hematocrit value, and the first voltage may be selected to be smaller than the second voltage.

Alternatively, in this embodiment, when the hematocrit value (the first biological information) represents a first hematocrit value in the memory 24, a first voltage is applied to the second input terminal and the third input terminal in the pre-processing application mode, when the hematocrit value represents a second hematocrit value in the memory 24, a second voltage is applied to the second input terminal and the third input terminal in the pre-processing application mode, and when the hematocrit value represents a third hematocrit value in the memory 24, a third voltage is applied to the second input terminal and the third input terminal in the pre-processing application mode. The first hematocrit value may be selected to be larger than the second hematocrit value and the third hematocrit value, and the second hematocrit value may be selected to be larger than the third hematocrit value. The first voltage may be selected to be smaller than the second voltage and the third voltage, and the second voltage may be selected to be smaller than the third voltage.

Next, in this embodiment, the control portion 19 applies the voltage that has been determined according to the measured hematocrit value (the first biological information) between the blood component measurement working electrode 6 and the blood component measurement counter electrode 7, e.g., for a predetermined time of 0.5 to 4.0 seconds (for 2.0 seconds in this embodiment) in the pre-processing application mode B (S9: "Apply determined voltage between measurement working electrode and measurement counter electrode" in FIG. 22).

Thereafter, in this embodiment, the control portion 19 stops the application of the voltage to all the electrodes (the hematocrit measurement working electrode 5, the blood component measurement working electrode 6, the blood component measurement counter electrode 7, and the blood component introduction detecting electrode 8) of the biosensor 2 for about 0.1 to 5.0 seconds (for 1.0 second in this embodiment) in order to further accelerate the reaction between the glucose in the blood and the reagent 11 containing the oxidoreductase and the electron carrier in the voltage application stop mode C (S10: "Stop voltage application" in FIG. 22).

Then, in the voltage application stop mode C, the glucose in the blood reacts with the oxidoreductase for a certain period of time.

In the next second biological information measurement mode D, the control portion 19 applies a voltage between the blood component measurement working electrode 6 and the blood component measurement counter electrode 7, oxidizes the reduced electron carrier that is generated on the blood component measurement working electrode 6 by the enzyme reaction, and detects the oxidation current, thereby measuring a glucose (blood glucose) value (the second biological information).

The reaction time between the glucose and the oxidoreductase in the second biological information measurement mode D is, e.g., 0.5 to 20 seconds, and more preferably 0.5 to 10 seconds. In this embodiment, the voltage application time during which a voltage is applied between the blood component measurement counter electrode 7 and the blood component measurement working electrode 6 in the second biological information measurement mode D can be changed based on the first biological information (the hematocrit value) in the first biological information measurement mode A.

Specifically, in this embodiment, a voltage of 0.05 to 1.0 V, and more preferably a voltage of 0.1 to 0.8 V (0.25 V in this embodiment) is applied between the blood component measurement working electrode 6 and the blood component measurement counter electrode 7 while the voltage application time can be changed based on the first biological information (the hematocrit value) in the first biological information measurement mode A (S11: "Apply voltage finally between measurement working electrode and measurement counter electrode" in FIG. 22).

Specifically, when the first biological information, i.e., the hematocrit value is 20% in the first biological information measurement mode A, the voltage application time is 2.0 seconds, during which a voltage is applied between the blood component measurement counter electrode 7 and the blood component measurement working electrode 6 in the second biological information measurement mode D.

When the hematocrit value is 45%, the voltage application time is 1.0 second, during which a voltage is applied between the blood component measurement counter electrode 7 and the blood component measurement working electrode 6 in the second biological information measurement mode D.

When the hematocrit value is 60%, the voltage application time is 0.8 seconds, during which a voltage is applied between the blood component measurement counter electrode 7 and the blood component measurement working electrode 6 in the second biological information measurement mode D.

In this embodiment, when the hematocrit value (the first biological information) represents a first hematocrit value in the memory 24, a fourth voltage is applied to the second input terminal and the third input terminal for a first period of time in the second biological information measurement mode, and when the hematocrit value represents a second hematocrit value in the memory 24, a fourth voltage is applied to the second input terminal and the third input terminal for a second period of time in the second biological information measurement mode. The first hematocrit value may be selected to be larger than the second hematocrit value, and the second period of time may be selected to be longer than the first period of time.

Alternatively, in this embodiment, when the hematocrit value (the first biological information) represents a first hematocrit value in the memory 24, a fourth voltage is applied to the second input terminal and the third input terminal for a first period of time in the second biological information measurement mode, when the hematocrit value represents a second hematocrit value in the memory 24, a fourth voltage is applied to the second input terminal and the third input terminal for a second period of time in the second biological information measurement mode, and when the hematocrit value represents a third hematocrit value in the memory 24, a fourth voltage is applied to the second input terminal and the third input terminal for a third period of time in the second biological information measurement mode. The first hematocrit value may be selected to be larger than the second hematocrit value and the third hematocrit value, and the second hematocrit value may be selected to be larger than the third hematocrit value. The second period of time and the third period of time may be selected to be longer than the first period of time, and the third period of time may be selected to be longer than the second period of time.

Thereafter, in this embodiment, the control portion 19 calculates the glucose value (the second biological information).

The calculated glucose value (the second biological information) is subjected to a conventionally known temperature correction (S12: "Measure and Correct glucose value in determined final application time" in FIG. 22).

The temperature correction is performed because the enzyme reaction for measuring the glucose value is affected by the ambient temperature. However, in the step S8 of determining a pre-processing voltage to be applied according to the hematocrit value, as shown in FIG. 3, if the voltage to be applied and/or the application time according to the hematocrit value are modified by the ambient temperature, the glucose value may be either corrected or not corrected at this stage. On the other hand, in the step S8 of determining a pre-processing voltage to be applied according to the hematocrit value, as shown in FIG. 3, if the voltage to be applied and the application time according to the hematocrit value are not modified by the ambient temperature, the glucose value needs to be corrected at this stage.

The glucose value thus corrected is displayed on the display portion 22 as a final glucose (blood glucose) value (the second biological information) (S13: "Display glucose value" in FIG. 22).

One of the characteristics of this embodiment is that the voltage to be applied in the pre-processing application mode B can be changed based on the oxidation current (which has been converted to a voltage value) that depends on the hematocrit value (the first biological information) and is recognized by the control portion 19, and that the voltage application time in the second biological information measurement mode D can be changed based on the first biological information (the hematocrit value) in the first biological information measurement mode A. Consequently, the blood glucose level displayed on the display portion 22 can achieve extremely high accuracy.

Hereinafter, this point will be described with reference to FIGS. 11 to 21.

Figure 18:
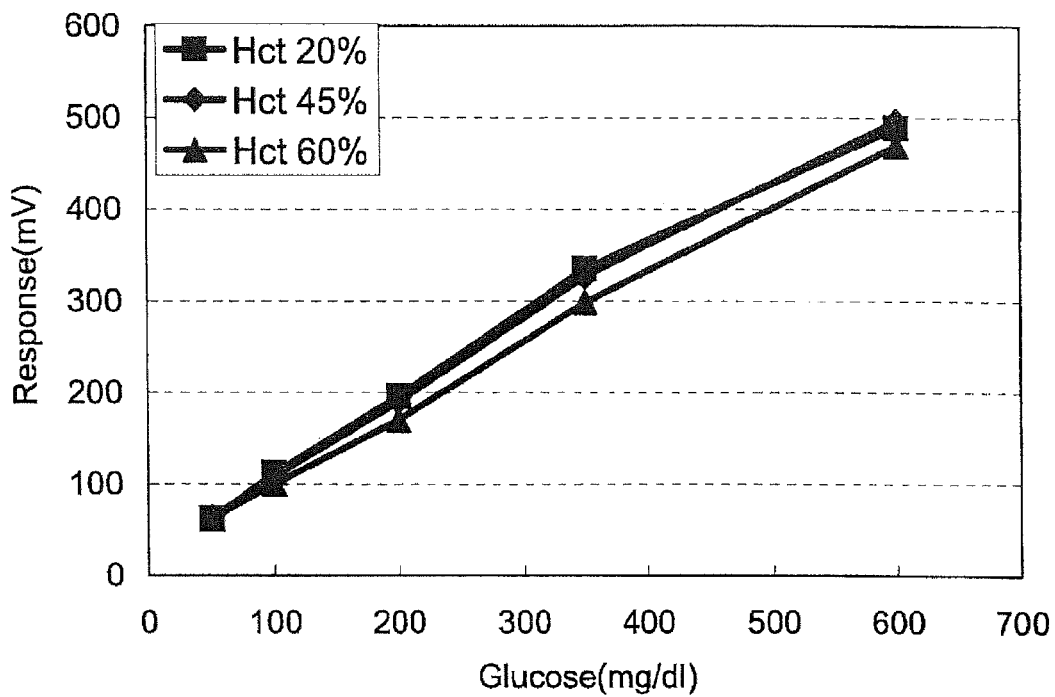
FIG. 18 is a graph showing a change in an output voltage (mV) with a blood glucose level in a biological information measurement device of another embodiment of the present invention.

FIG. 18 is a graph showing a change in an output voltage (mV) with a blood glucose level in a biological information measurement device of another embodiment of the present invention. Specifically, in this embodiment, FIG. 18 illustrates how the output of the A/D converter 20 (FIG. 1) is changed with the blood glucose level in the second biological information measurement mode D when the hematocrit values are 20%, 45%, and 60% (corresponding to the state before the correction in the step S12 in FIG. 22). As can be seen from FIG. 18, the output voltage increases with increasing the blood glucose level no matter whether the hematocrit value is 20%, 45%, or 60%.

On the other hand, FIG. 11 is a graph showing a change in an output voltage (mV) with a blood glucose level in a biological information measurement device of a conventional example. Specifically, in the conventional example, FIG. 11 illustrates how the output of the A/D converter 20 (FIG. 1) is changed with the blood glucose level in the second biological information measurement mode D when the hematocrit values are 20%, 45%, and 60%. As can be seen from FIG. 11, similarly to FIG. 18, the output voltage increases with increasing the blood glucose level no matter whether the hematocrit value is 20%, 45%, or 60%.

Comparing FIG. 18 (this embodiment) and FIG. 11 (the conventional example) shows that a variation in the detected blood glucose level (the second biological information) is small even if the hematocrit values (the first biological information) differ in this embodiment. For example, in FIG. 11 (the conventional example), when the blood glucose level is 350 mg/dl, the output voltage is 280 mV for a hematocrit value of 45%, but the output voltage is increased to 390 mV for a hematocrit value of 20%, resulting in a difference of 110 mV.

Moreover, in FIG. 11 (the conventional example), while the output voltage is 280 mV for a hematocrit value of 45%, the output voltage is reduced to 200 mV for a hematocrit value of 60%, resulting in a difference of 80 mV.

On the other hand, in FIG. 18 (this embodiment), when the blood glucose level is 350 mg/dl, the output voltage is 330 mV for a hematocrit value of 45%, and the output voltage is 330 mV for a hematocrit value of 20%, making no difference.

Moreover, in FIG. 18 (this embodiment), while the output voltage is 330 mV for a hematocrit value of 45%, the output voltage is 300 mV for a hematocrit value of 60%, making only a difference of 30 mV.

As a result of not only changing the voltage to be applied between the blood component measurement working electrode 6 and the blood component measurement counter electrode 7 in the pre-processing application mode B, as shown in FIG. 15, but also changing the voltage application time in the second biological information measurement mode D, this embodiment can reduce a difference in the output voltage between the hematocrit values.

In other words, this embodiment deals with the following points. As described above, if blood has a high hematocrit value (high Hct value), the viscosity of the blood is increased and the current response is relatively reduced during the measurement of the glucose. Therefore, the high-Hct blood requires a voltage to achieve a high current response. If blood has a low hematocrit value (low Hct value), the viscosity of the blood is reduced and the current response is relatively increased during the measurement of the glucose. Therefore, the low-Hct blood requires a voltage to achieve a low current response.

In contrast, the conventional example applies the same voltage between the blood component measurement working electrode 6 and the blood component measurement counter electrode 7 in the pre-processing application mode B regardless of the hematocrit value (FIG. 11), so that the output voltage varies greatly. FIG. 11 is a graph showing a change in an output voltage (mV) with a blood glucose level in a biological information measurement device of the conventional example.

FIG. 12 is a graph showing a difference in sensitivity of an output voltage (mV) with respect to a hematocrit value in a biological information measurement device of the conventional example. Specifically, FIG. 12 illustrates a difference (the degree of influence) in each of the samples with blood glucose levels of 100 mg/dl and 350 mg/dl when their hematocrit values are 20% and 60% as compared to 45% in the conventional example.

FIG. 12 (the conventional example) shows that both the samples with blood glucose levels of 100 mg/dl and 350 mg/dl have a difference of 35% or more on the hematocrit 20% side and a difference of 20% or more on the hematocrit 60% side from the hematocrit value 45%.

Thus, in the conventional example, the output voltage of the A/D converter 20 varies greatly depending on the hematocrit value, as can be seen from FIGS. 11 and 12.

The conventional example also has made an attempt to calculate the final blood glucose level by correcting the output voltage of the A/D converter 20 in accordance with the subsequently detected hematocrit value.

However, in this conventional example, as shown in FIG. 13, the sample with a blood glucose level of 100 mg/dl has a variation of +7.5% to −4.0% when the hematocrit value is 20%, a variation of +9.0% to −5.0% when the hematocrit value is 45%, and a variation of +9.5% to −7.0% when the hematocrit value is 60%. FIG. 13 is a graph showing a difference in sensitivity of an output voltage (mV) with respect to a hematocrit value in a biological information measurement device of the conventional example.

As shown in FIG. 14, the sample with a blood glucose level of 350 mg/dl has a variation of +8.0% to −4.0% when the hematocrit value is 20%, a variation of +10.0% to −6.0% when the hematocrit value is 45%, and a variation of +11.0% to −7.5% when the hematocrit value is 60%. FIG. 14 is a graph showing a difference in sensitivity of an output voltage (mV) with respect to a hematocrit value in a biological information measurement device of the conventional example.

Even if subsequent corrections are performed while there is such a great variation, the final blood glucose level will still vary significantly.

Thus, the measurement accuracy is low in the conventional biological information measurement device.

Figure 19:
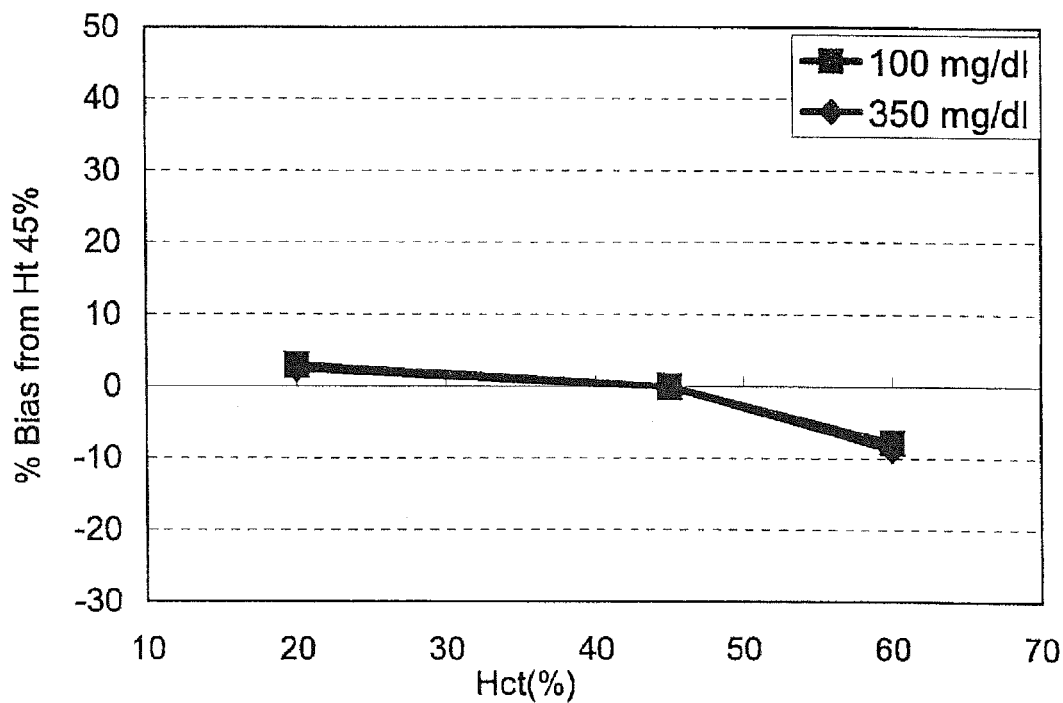
FIG. 19 is a graph showing a difference in sensitivity of an output voltage (mV) with respect to a hematocrit value in a biological information measurement device of another embodiment of the present invention.

Contrary to the conventional example, FIG. 19 is a graph showing a difference in sensitivity of an output voltage (mV) with respect to a hematocrit value in a biological information measurement device of this embodiment. Specifically, FIG. 19 illustrates a difference (the degree of influence) in each of the samples with blood glucose levels of 100 mg/dl and 350 mg/dl when their hematocrit values are 20% and 60% as compared to 45% in this embodiment.

FIG. 19 (this embodiment) shows that both the samples with blood glucose levels of 100 mg/dl and 350 mg/dl have only a difference of about 2% on the hematocrit 20% side and only a difference of about 9% on the hematocrit 60% side from the hematocrit value 45%.

Thus, in this embodiment, the output voltage of the A/D converter 20 varies slightly depending on the hematocrit value, as can be seen from FIGS. 18 and 19.

Therefore, this embodiment shows only a small variation when the final blood glucose level is calculated from the output voltage of the A/D converter 20.

Figure 20:
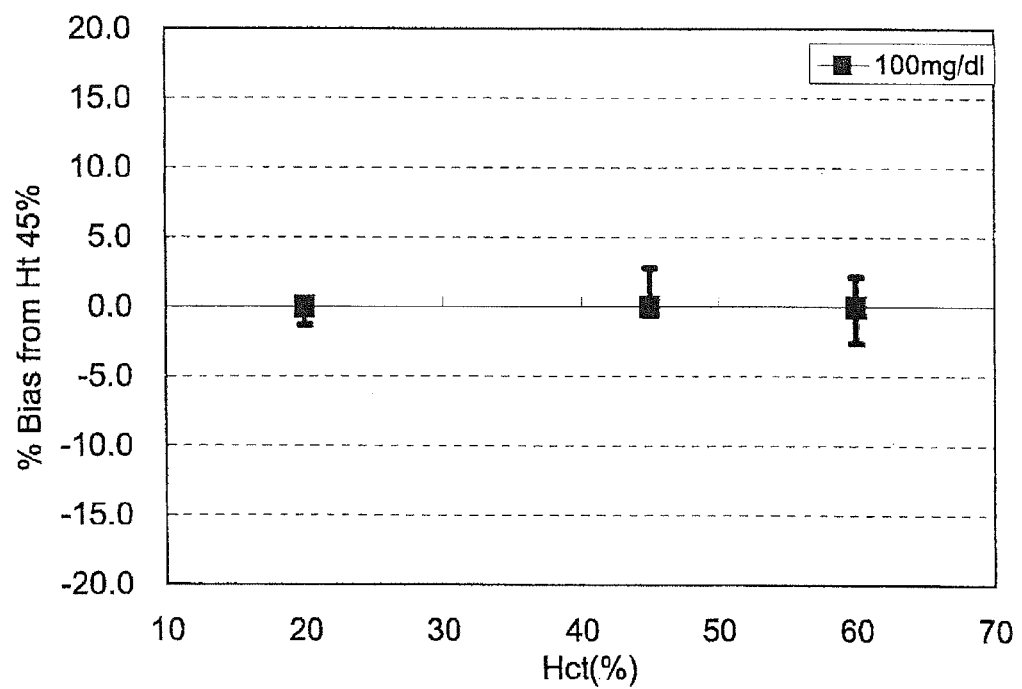
FIG. 20 is a graph showing a difference in sensitivity of an output voltage (mV) with respect to a hematocrit value in a biological information measurement device of another embodiment of the present invention.
Figure 21:
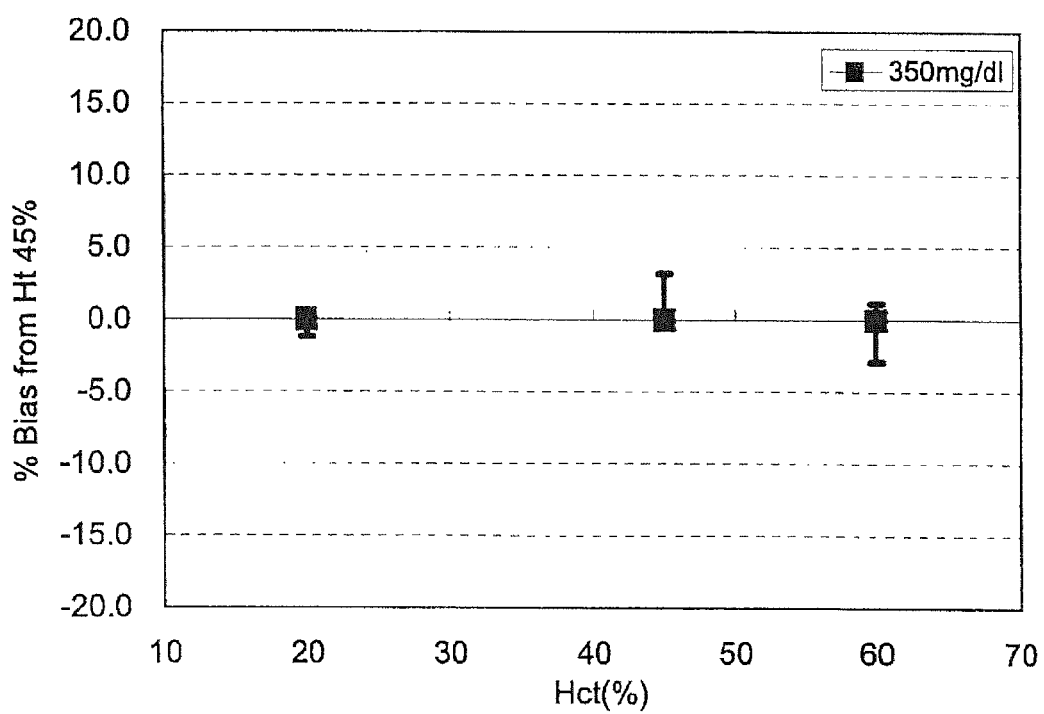
FIG. 21 is a graph showing a difference in sensitivity of an output voltage (mV) with respect to a hematocrit value in a biological information measurement device of another embodiment of the present invention.

This point will be further described with reference to FIGS. 20 and 21. FIGS. 20 and 21 are graphs showing a difference in sensitivity of an output voltage (mV) with respect to a hematocrit value in a biological information measurement device of this embodiment. As shown in FIG. 20, the sample with a blood glucose level of 100 mg/dl has substantially no variation when the hematocrit value is 20%, only a variation of +2.5% to 0.0% when the hematocrit value is 45%, and only a variation of +2.5% to −2.5% when the hematocrit value is 60%.

As shown in FIG. 21, the sample with a blood glucose level of 350 mg/dl has substantially no variation when the hematocrit value is 20%, only a variation of +3.0% to 0.0% when the hematocrit value is 45%, and only a variation of +0.0% to −3.0% when the hematocrit value is 60%.

Therefore, in this embodiment, since the blood glucose level itself is measured under the conditions that are not much affected by the hematocrit value, the measurement accuracy can be improved.

This embodiment performs a temperature correction in the step S12 in FIG. 22 in order to reduce the influence of the temperature, so that the measurement accuracy can be improved further.

In this embodiment, if the resultant hematocrit value (the first biological information) is a standard value (e.g., the hematocrit value is 42), it is not necessary to change the voltage to be applied in the pre-processing application mode B and the voltage application time in the second biological information measurement mode D.

Embodiment 3

Embodiment 1 can change a voltage to be applied in the pre-processing application mode B, and Embodiment 2 can change a voltage to be applied in the pre-processing application mode B and an application time in the second biological information measurement mode D. Using the configurations shown in FIGS. 1 and 2, the control portion 19 may perform a control operation as shown in FIG. 23.

Figure 23:
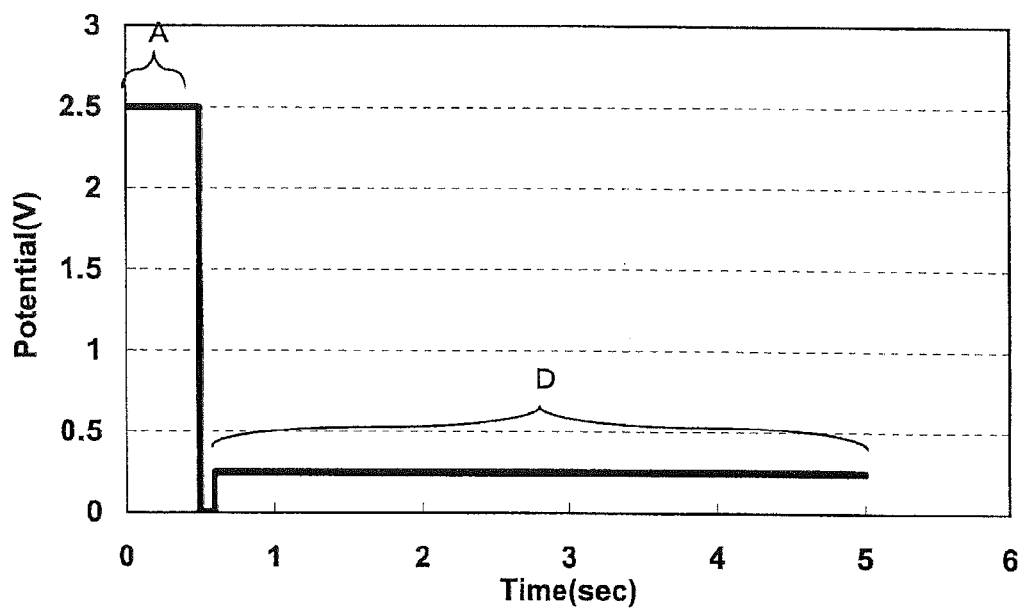
FIG. 23 is a diagram showing the state of a voltage applied over time in a biological information measurement device of yet another embodiment of the present invention.

FIG. 23 is a diagram showing the state of a voltage applied over time in a biological information measurement device of yet another embodiment of the present invention. The control operation shown in FIG. 23 mainly performs the first biological information measurement mode A and the second biological information measurement mode D.

Specifically, in this embodiment, a hematocrit value (the first biological information) is measured in the first biological information measurement mode A, and then the second biological information measurement mode D is performed immediately after a short interval (which is shorter than the stop time of the voltage application stop mode C in Embodiments 1 and 2). In performing the second biological information measurement mode D, based on the hematocrit value (the first biological information) measured in the first biological information measurement mode A, the control portion 19 can change a voltage value to be applied to the blood component measurement counter electrode 7 and the blood component measurement working electrode 6 in the second biological information measurement mode D, or further can change a voltage application time during which a voltage is applied to the blood component measurement counter electrode 7 and the blood component measurement working electrode 6 in the second biological information measurement mode D.

Figure 24:
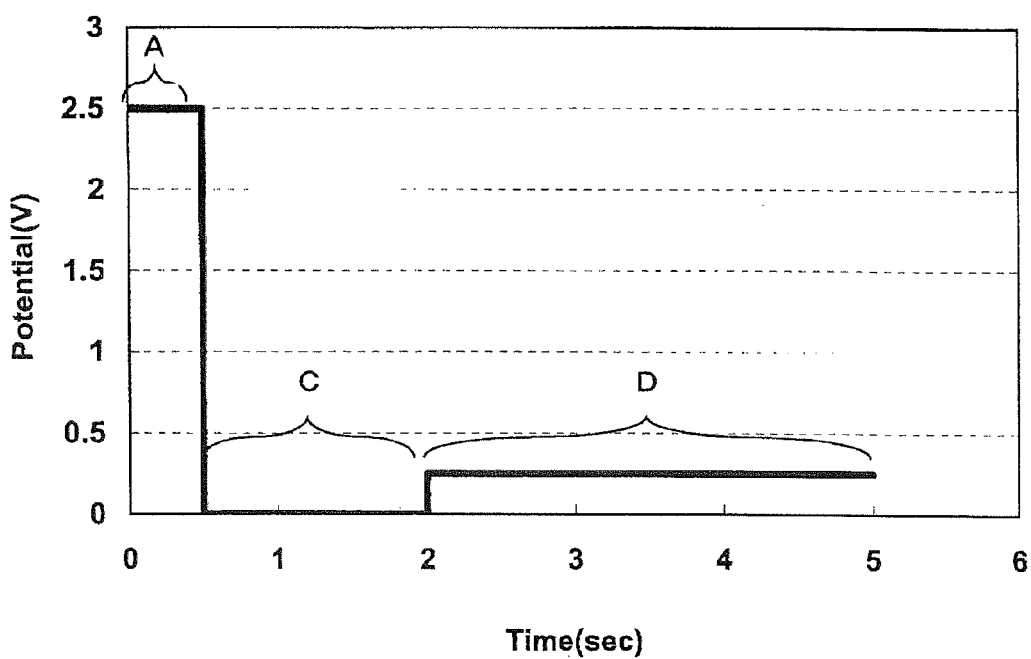
FIG. 24 is a diagram showing the state of a voltage applied over time in a biological information measurement device of yet another embodiment of the present invention.

FIG. 24 is a diagram showing the state of a voltage applied over time in a biological information measurement device of yet another embodiment of the present invention. The control operation shown in FIG. 24, which is yet another embodiment of the present invention, performs the first biological information measurement mode A, the voltage application stop mode C, and the second biological information measurement mode D.

Specifically, in this embodiment, a hematocrit value (the first biological information) is measured in the first biological information measurement mode A, and then the voltage application stop mode C is performed to stop the application of the voltage to the blood component measurement counter electrode 7 and the blood component measurement working electrode 6, and subsequently the second biological information measurement mode D is performed. In performing the second biological information measurement mode D, based on the hematocrit value (the first biological information) measured in the first biological information measurement mode A, the control portion 19 can change a voltage value to be applied to the blood component measurement counter electrode 7 and the blood component measurement working electrode 6 in the second biological information measurement mode D, or further can change a voltage application time during which a voltage is applied to the blood component measurement counter electrode 7 and the blood component measurement working electrode 6 in the second biological information measurement mode D, or still further can change a stop time during which the application of the voltage to all the electrodes (the hematocrit measurement working electrode 5, the blood component measurement working electrode 6, the blood component measurement counter electrode 7, and the blood component introduction detecting electrode 8) is stopped in the voltage application stop mode C.

Figure 25:
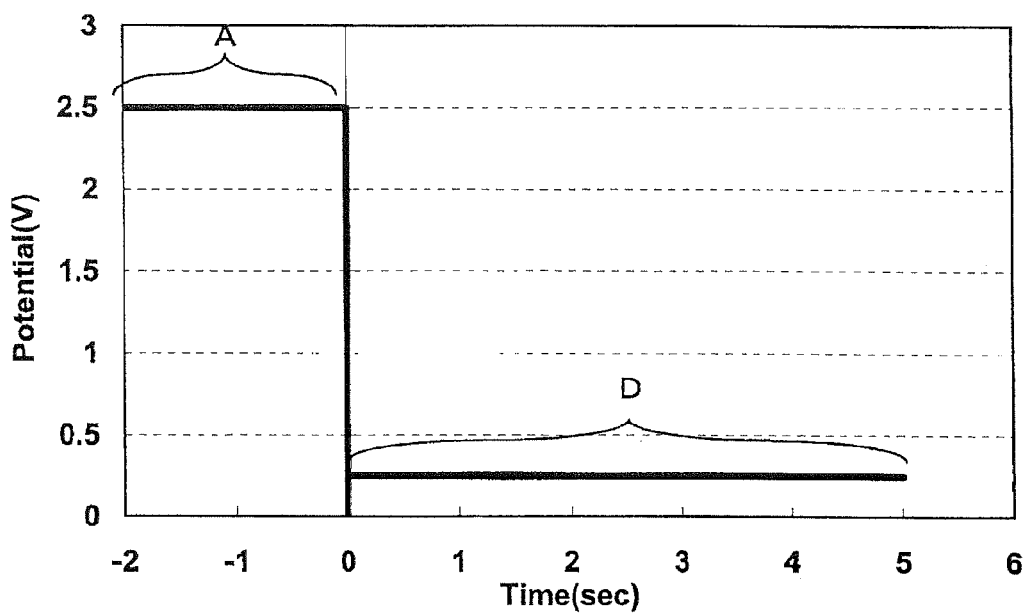
FIG. 25 is a diagram showing the state of a voltage applied over time in a biological information measurement device of yet another embodiment of the present invention.

FIG. 25 is a diagram showing the state of a voltage applied over time in a biological information measurement device of yet another embodiment of the present invention. The control operation shown in FIG. 25, which is yet another embodiment of the present invention, performs the first biological information measurement mode A and the second biological information measurement mode D.

Specifically, in this embodiment, before starting the measurement (i.e., at the time of waiting for the detection of blood), a hematocrit value (the first biological information) is measured in the first biological information measurement mode A, and the second biological information measurement mode D is performed immediately. In performing the second biological information measurement mode D, based on the hematocrit value (the first biological information) measured in the first biological information measurement mode A, the control portion 19 can change a voltage value to be applied to the blood component measurement counter electrode 7 and the blood component measurement working electrode 6 in the second biological information measurement mode D, or further can change a voltage application time during which a voltage is applied to the blood component measurement counter electrode 7 and the blood component measurement working electrode 6 in the second biological information measurement mode D.

Figure 26:
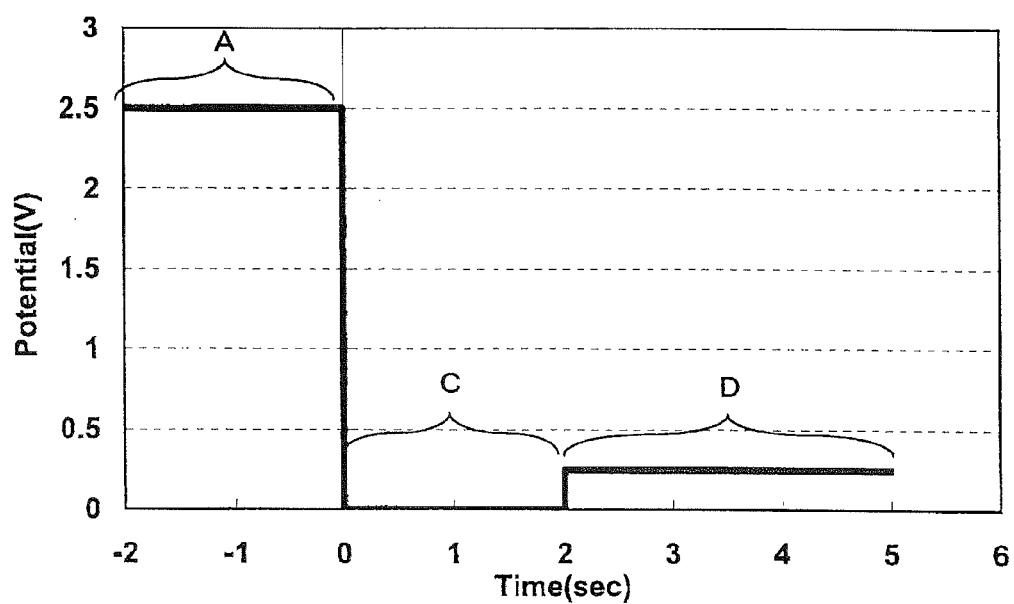
FIG. 26 is a diagram showing the state of a voltage applied over time in a biological information measurement device of yet another embodiment of the present invention.

FIG. 26 is a diagram showing the state of a voltage applied over time in a biological information measurement device of yet another embodiment of the present invention. The control operation shown in FIG. 26, which is yet another embodiment of the present invention, performs the first biological information measurement mode A, the voltage application stop mode C, and the second biological information measurement mode D.

Specifically, in this embodiment, before starting the measurement (i.e., at the time of waiting for the detection of blood), a hematocrit value (the first biological information) is measured in the first biological information measurement mode A, and then (when the measurement is started) the voltage application stop mode C is performed to stop the application of the voltage to the blood component measurement counter electrode 7 and the blood component measurement working electrode 6, and subsequently the second biological information measurement mode D is performed. In performing the second biological information measurement mode D, based on the hematocrit value (the first biological information) measured in the first biological information measurement mode A, the control portion 19 can change a voltage value to be applied to the blood component measurement counter electrode 7 and the blood component measurement working electrode 6 in the second biological information measurement mode D, or further can change a voltage application time during which a voltage is applied to the blood component measurement counter electrode 7 and the blood component measurement working electrode 6 in the second biological information measurement mode D, or still further can change a stop time during which the application of the voltage to all the electrodes (the hematocrit measurement working electrode 5, the blood component measurement working electrode 6, the blood component measurement counter electrode 7, and the blood component introduction detecting electrode 8) is stopped in the voltage application stop mode C.

Figure 27:
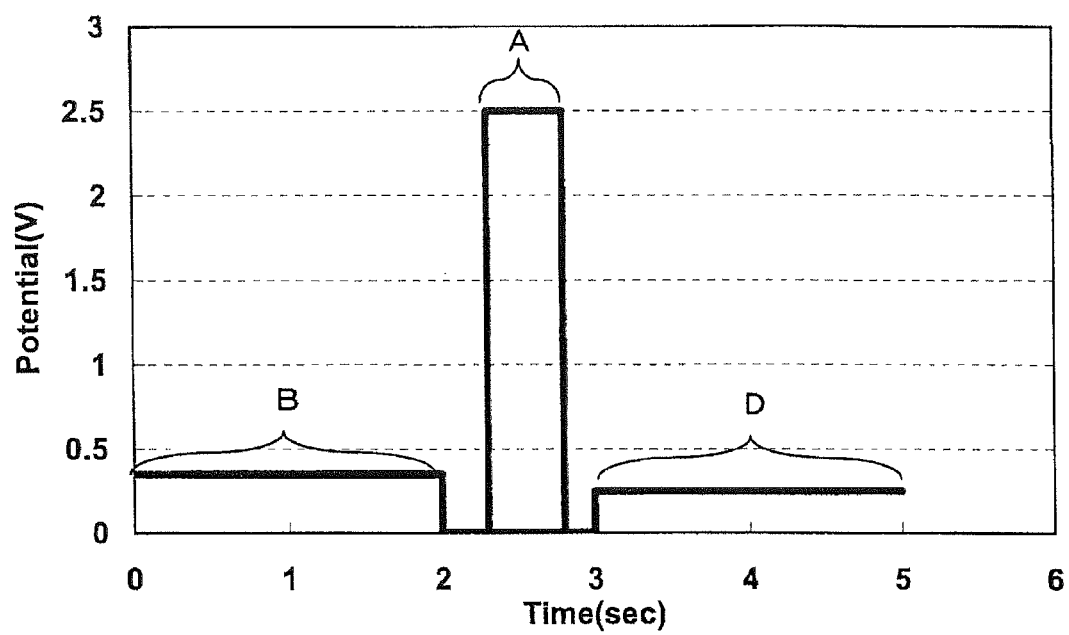
FIG. 27 is a diagram showing the state of a voltage applied over time in a biological information measurement device of yet another embodiment of the present invention.

FIG. 27 is a diagram showing the state of a voltage applied over time in a biological information measurement device of yet another embodiment of the present invention. The control operation shown in FIG. 27, which is yet another embodiment of the present invention, performs the pre-processing application mode B, the first biological information measurement mode A, the voltage application stop mode C, and the second biological information measurement mode D.

Specifically, in this embodiment, an approximate glucose value is calculated in the pre-processing application mode B, and then based on the hematocrit value (the first biological information) in the first biological information measurement mode A, the control portion 19 can change a voltage value to be applied to the blood component measurement counter electrode 7 and the blood component measurement working electrode 6 in the second biological information measurement mode D and a voltage application time during which a voltage is applied to the blood component measurement counter electrode 7 and the blood component measurement working electrode 6 in the second biological information measurement mode D. Moreover, the voltage application stop mode C or a short interval (which is shorter than the stop time of the voltage application stop mode C in Embodiments 1 and 2) may be provided before and after the first biological information measurement mode A.

In this embodiment, if the resultant hematocrit value (the first biological information) is a standard value (e.g., the hematocrit value is 42), it is not necessary to change the voltage to be applied and the voltage application time in the second biological information measurement mode D.

INDUSTRIAL APPLICABILITY

As described above, the present invention is directed to a biological information measurement device to which a biosensor is to be attached. The biosensor includes a first electrode, a second electrode, a third electrode, and a reagent portion provided between the second electrode and the third electrode. The biological information measurement device includes the following: a first input terminal to be connected to the first electrode; a second input terminal to be connected to the second electrode; a third input terminal to be connected to the third electrode; a voltage application portion that applies a voltage to the first input terminal, the second input terminal, and the third input terminal; a determination portion that is connected to the first input terminal, the second input terminal, and the third input terminal; a control portion that is connected to the determination portion and the voltage application portion; and a display portion that is connected to the control portion. The control portion is configured to perform a first biological information measurement mode in which first biological information is measured based on a current flowing through the first input terminal and a second biological information measurement mode in which second biological information is measured by applying a voltage to the second input terminal and the third input terminal after the first biological information measurement mode. The display portion is configured to display the second biological information. The control portion is configured to be able to change at least one of i) a voltage value to be applied to the second input terminal and the third input terminal in the second biological information measurement mode and ii) a voltage application time during which a voltage is applied to the second input terminal and the third input terminal in the second biological information measurement mode based on the first biological information in the first biological information measurement mode. Thus, the present invention can improve the measurement accuracy.

According to the present invention, at least one of the voltage value to be applied to the second input terminal and the third input terminal in the second biological information measurement mode and the voltage application time during which a voltage is applied to the second input terminal and the third input terminal in the second biological information measurement mode can be changed based on the first biological information in the first biological information measurement mode. For example, a hematocrit value is measured in the first biological information measurement mode, and the biological information, e.g., a blood glucose level is measured based on this hematocrit value in the second biological information measurement mode.

As described above, the present invention is directed to a biological information measurement device to which a biosensor is to be attached. The biosensor includes a first electrode, a second electrode, a third electrode, and a reagent portion provided between the second electrode and the third electrode. The biological information measurement device includes the following: a first input terminal to be connected to the first electrode; a second input terminal to be connected to the second electrode; a third input terminal to be connected to the third electrode; a voltage application portion that applies a voltage to the first input terminal, the second input terminal, and the third input terminal; a determination portion that is connected to the first input terminal, the second input terminal, and the third input terminal; a control portion that is connected to the determination portion and the voltage application portion; and a display portion that is connected to the control portion. The control portion is configured to perform a first biological information measurement mode in which first biological information is measured based on a current flowing through the first input terminal, a pre-processing application mode in which a voltage is applied to the second input terminal and the third input terminal after the first biological information measurement mode, a voltage application stop mode in which the application of the voltage to the second input terminal and the third input terminal is stopped after the pre-processing application mode, and a second biological information measurement mode in which second biological information is measured by applying a voltage to the second input terminal and the third input terminal after the voltage application stop mode. The display portion is configured to display the second biological information. The control portion is configured to be able to change a voltage value to be applied to the second input terminal and the third input terminal in the pre-processing application mode based on the first biological information in the first biological information measurement mode. Thus, the present invention can improve the measurement accuracy.

According to the present invention, the voltage value to be applied to the second input terminal and the third input terminal in the pre-processing application mode can be changed based on the first biological information in the first biological information measurement mode. For example, a hematocrit value is measured in the first biological information measurement mode, and the biological information, e.g., a blood glucose level is measured based on this hematocrit value in the second biological information measurement mode.

As described above, the present invention is directed to a biological information measurement device to which a biosensor is to be attached. The biosensor includes a first electrode, a second electrode, a third electrode, and a reagent portion provided between the second electrode and the third electrode. The biological information measurement device includes the following: a first input terminal to be connected to the first electrode; a second input terminal to be connected to the second electrode; a third input terminal to be connected to the third electrode; a voltage application portion that applies a voltage to the first input terminal, the second input terminal, and the third input terminal; a determination portion that is connected to the first input terminal, the second input terminal, and the third input terminal; a control portion that is connected to the determination portion and the voltage application portion; and a display portion that is connected to the control portion. The control portion is configured to perform a first biological information measurement mode in which first biological information is measured based on a current flowing through the first input terminal, a pre-processing application mode in which a voltage is applied to the second input terminal and the third input terminal after the first biological information measurement mode, a voltage application stop mode in which the application of the voltage to the second input terminal and the third input terminal is stopped after the pre-processing application mode, and a second biological information measurement mode in which second biological information is measured by applying a voltage to the second input terminal and the third input terminal after the voltage application stop mode. The display portion is configured to display the second biological information. The control portion is configured to be able to change a voltage value to be applied to the second input terminal and the third input terminal in the pre-processing application mode based on the first biological information in the first biological information measurement mode. The control portion is configured to be able to change a voltage application time during which a voltage is applied to the second input terminal and the third input terminal in the second biological information measurement mode based on the first biological information in the first biological information measurement mode. Thus, the present invention can improve the measurement accuracy.

According to the present invention, the voltage value to be applied to the second input terminal and the third input terminal in the pre-processing application mode can be changed based on the first biological information in the first biological information measurement mode, and the voltage application time during which a voltage is applied to the second input terminal and the third input terminal in the second biological information measurement mode can be changed based on the first biological information in the first biological information measurement mode. For example, a hematocrit value is measured in the first biological information measurement mode, and the biological information, e.g., a blood glucose level is measured based on this hematocrit value in the second biological information measurement mode.

Therefore, according to the present invention, since the blood glucose level itself is measured under the conditions that are not much affected by the hematocrit value, the measurement accuracy can be improved.

It is expected that the present invention will be used as a biological information detector for detecting the biological information such as a blood glucose level.

DESCRIPTION OF REFERENCE NUMERALS

1 Main body case
2 Biosensor
3 Insertion port
4 Insulating substrate
5 Hematocrit measurement working electrode
6 Blood component measurement working electrode
7 Blood component measurement counter electrode
8 Blood component introduction detecting electrode
9 Input terminal portion
10 Reagent portion
11 Reagent
12 Spacer
13 Cover
14 Blood supply path
15 Blood inlet
16 Air hole
17 Voltage application portion
18 Current-voltage converter
19 Control portion
20 A/D converter
21 Determination portion
22 Display portion
23 Power source
24 Memory
25 Clock
26 Correction portion

The invention claimed is:

1. A biological information measurement device to which a biosensor is to be attached, the biosensor comprising a first electrode, a second electrode, a third electrode, and a reagent portion provided between the second electrode and the third electrode, the biological information measurement device comprising:
a first input terminal to be connected to the first electrode;
a second input terminal to be connected to the second electrode;
a third input terminal to be connected to the third electrode;
a voltage application portion that applies a voltage to the first input terminal, the second input terminal, and the third input terminal; and
a control portion that is connected to the voltage application portion,
wherein the control portion is configured to perform a first biological information measurement mode, then a voltage application stop mode, and then a second biological information measurement mode,
in the first biological information measurement mode, first biological information is measured based on a current flowing through the first input terminal,
in the voltage application stop mode, the application of the voltage to the first, second and third input terminals are stopped, and
in the second biological information measurement mode, second biological information is measured by applying a voltage to the second input terminal and the third input terminal,
the first biological information is a hematocrit value,
when the hematocrit value represents a first hematocrit value, the control portion applies a first voltage to the second input terminal and the third input terminal in the second biological information measurement mode, or applies a voltage to the second input terminal and the third input terminal for a first application time in the second biological information measurement mode, and stops the application of the voltage in the voltage application stop mode for a first stop time,
when the hematocrit value represents a second hematocrit value, the control portion applies a second voltage to the second input terminal and the third input terminal in the second biological information measurement mode, or applies a voltage to the second input terminal and the third input terminal for a second application time in the second biological information measurement mode, and stops the application of the voltage in the voltage application stop mode for a second stop time,
the first hematocrit value is larger than the second hematocrit value,
the first voltage is smaller than the second voltage, and
the second application time is longer than the first application time.

2. The biological information measurement device according to claim 1, wherein a clock is connected to the control portion.

3. The biological information measurement device according to claim 1,
wherein a determination portion is connected to the control portion, and compares a current flowing between the second electrode and the third electrode through the second input terminal and the third input terminal with a threshold value.

* * * * *